US008043833B2

(12) United States Patent
Schwartz et al.

(10) Patent No.: US 8,043,833 B2
(45) Date of Patent: Oct. 25, 2011

(54) EXPRESSION OF SOLUBLE THERAPEUTIC PROTEINS

(75) Inventors: Marc F. Schwartz, West Windsor, NJ (US); Bingyuan Wu, Horsham, PA (US); Aliakbar Mobasseri, Voorhees, NJ (US); Shawn A. DeFrees, North Wales, PA (US); Tarik Soliman, Chester Springs, PA (US); Karl F. Johnson, Hatboro, PA (US)

(73) Assignee: Novo Nordisk A/S, Bagsvaerd (DK)

( * ) Notice: Subject to any disclaimer, the term of this patent is extended or adjusted under 35 U.S.C. 154(b) by 358 days.

(21) Appl. No.: 12/092,125

(22) PCT Filed: Sep. 6, 2006

(86) PCT No.: PCT/US2006/034844
§ 371 (c)(1),
(2), (4) Date: Oct. 14, 2008

(87) PCT Pub. No.: WO2007/055789
PCT Pub. Date: May 18, 2007

(65) Prior Publication Data
US 2009/0298121 A1 Dec. 3, 2009

Related U.S. Application Data

(60) Provisional application No. 60/732,352, filed on Oct. 31, 2005.

(51) Int. Cl.
C12P 21/04 (2006.01)
C12P 21/06 (2006.01)
C12N 15/00 (2006.01)
A61K 1/00 (2006.01)
C07K 1/00 (2006.01)
A23J 1/00 (2006.01)

(52) U.S. Cl. ...... 435/71.2; 435/69.1; 435/440; 530/399; 530/350; 530/412

(58) Field of Classification Search .................. None
See application file for complete search history.

(56) References Cited

U.S. PATENT DOCUMENTS

| 4,965,199 | A | 10/1990 | Capon et al. |
| 6,027,888 | A | 2/2000 | Georgiou et al. |
| 6,753,165 | B1 | 6/2004 | Cox et al. |
| 6,872,563 | B1 | 3/2005 | Beckwith et al. |
| 6,903,077 | B1 * | 6/2005 | Heintz ............... 514/44 R |
| 2003/0099618 | A1 | 5/2003 | Couto et al. |
| 2003/0104628 | A1 | 6/2003 | Hua et al. |
| 2005/0186666 | A1 | 8/2005 | Schneider et al. |

FOREIGN PATENT DOCUMENTS

| WO | WO99/15636 | 4/1999 |
| WO | WO2004/103275 | 12/2004 |
| WO | WO2005/055946 | 6/2005 |
| WO | WO2005/070138 | 8/2005 |
| WO | WO2006/050247 | 5/2006 |
| WO | WO2006/103298 | 10/2006 |

OTHER PUBLICATIONS

Hanning et al. 1998. Trends in Biotech. 16:54-60.*
Wang et al. 2010. BMC Biotechnology 10:14.*
Takeshima K. et al., The preparation and phospholipid binding property of the C2 domain of human factor VIII., Thromb. Hemost. 2003, 89:788-94.
Suh J-K. et al., Yeast flavin-containing monooxygenase generates oxidizing equivalents that control protein folding in the endoplasmic reticulum., Proc. Natl. Acad. Sci. USA, vol. 96, pp. 2687-2691, Mar. 1999.
Sahdev S. et al., Production of active eukaryotic proteins through bacterial expression systems: a review of the existing biotechnology strategies., Mol. Cell. Biochem., 2008, 307:249-264.
Toole J. S. et al., Molecular cloning of a cDNA encoding human antihaemophilic factor., Nature , Nov. 22, 1984, 312: 342-347.
Bessette, et al. "Efficient folding of proteins with multiple disulfide bonds in the *Escherichia coli* cytoplasm," *PNAS* 96:13703-13708 (1999).
Choy and Davidson, "Gaucher's disease II. Studies on the kinetics of β-glucosidase and the effects of sodium taurocholate in normal and Gaucher tissues," *Pediat. Res.* 14:54-59 (1980).
Choy, "Gaucher disease: the effects of phosphatidylserine on glucocerebrosidase from normal and Gaucher fibroblasts," *Hum. Genet.* 67:432-436 (1984).
Ferrer et al., "Chaperonins govern growth of *Escherichia coli* at low temperatures," *Nat. Biotechnol.* 21:1266-1267 (2003).
Frand et al., "Pathways for protein disulphide bond formation," *Trends in Cell Biol.* 10:203-210 (2000).
Hwang et al., "Oxidized redox state of glutathione in the endoplasmic reticulum," *Science* 257:1496-1502 (1992).
Jurado et al., "Production of functional single-chain Fv antibodies in the cytoplasm of *Escherichia coli*," *J. Mol. Biol.* 320:1-10 (2002).
Kharitonenkov, A. et al., "FGF-21 as a novel metabolic regulator," *J. Clin. Invest.* 115:1627-1635 (2005).
Levy et al., "Production of Correctly Folded Fab Antibody Fragment in the Cytoplasm of *Escherichia coli* trxB gor Mutants via the Coexpression of Molecular Chaperones," *Protein Expression and Purification* 23:338-347 (2001).
Ostergaard, et al., "Monitoring disulfide bond formation in the eukaryotic cytosol," *J. Cell Biol.* 166:337-345 (2004).
Patra, et al., "Optimization of inclusion body solubilization and renaturation of recombinant human growth hormone from *Escherichia coli*," *Protein Expr. Purif.* 18:182-192 (2000).
Prinz et al., "The role of the thioredoxin and glutaredoxin pathways in reducing protein disulfide bonds in the *Escherichia coli* cytoplasm," *J. Biol Chem.* 272:15661-15667 (1997).
Sorensen and Mortensen, "Microbial cell factories: Soluble expression of recombinant proteins in the cytoplasm of *Escherichia coli*," *BioMed Central* 4:1-8 (2005).

(Continued)

*Primary Examiner* — Shulamith H Shafer
(74) *Attorney, Agent, or Firm* — Leydig, Voit & Mayer, Ltd.

(57) ABSTRACT

The present invention provides enhanced methods of producing soluble, active fibroblast growth factor-20 (FGF-20), FGF-21, neurotrophin-3 (NT-3), growth hormone (GH), granulocyte colony stimulating factor (G-CSF), or glucocerebrosidase proteins in microorganisms that have an oxidizing environment.

12 Claims, 11 Drawing Sheets

OTHER PUBLICATIONS

Tuggle and Fuchs, "Glutathione reductase is not required for maintenance of reduced glutathione in *Escherichia coli* K-12," *J. Bacteriol* 162:448-450 (1985).

"Novagen pET System Manual"; 10th Edition Rev. B 0403, 68 pages (2003).

"Novagen: 71352: Rosetta-gami™ 2(DE3)pLysS Competent Cells"; http://www.emdbiosciences.com/product/print/71352, 2 pages (2005).

"Novagen: 71431: Origami™ 2 Competent Cell Set"; http://www.emdbiosciences.com/product/71431, 2 pages (2005).

* cited by examiner

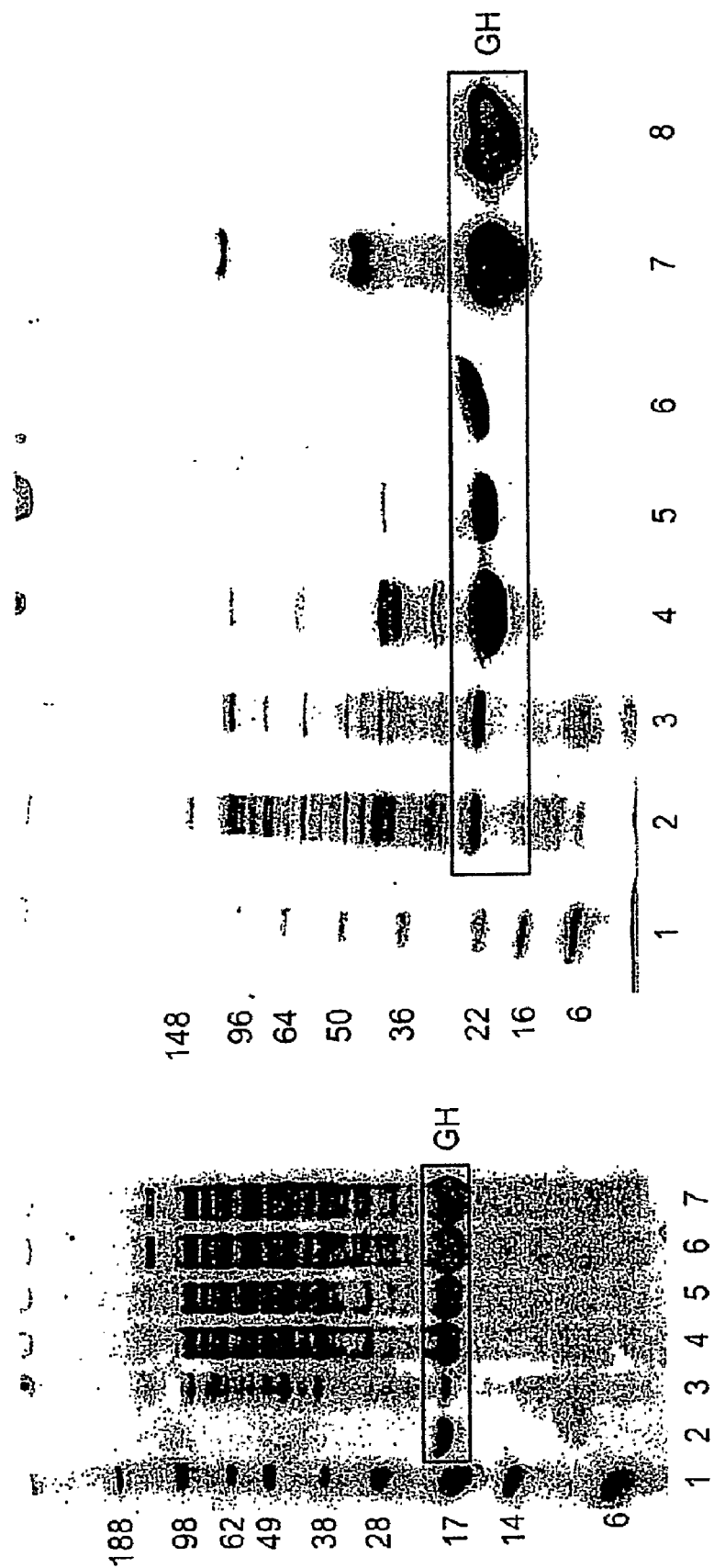

EXPRESSION OF SOLUBLE THERAPEUTIC PROTEINS

CROSS-REFERENCES TO RELATED APPLICATIONS

This application is a U.S. National Phase Application under 35 U.S.C. §371 of International Application No. PCT/US2006/034844, filed on Sep. 6, 2006, which claims the benefit of U.S. Provisional Application No. 60/732,352, filed Oct. 31, 2005, which is herein incorporated by reference for all purposes.

FIELD OF INVENTION

The present invention provides enhanced methods of producing soluble, active fibroblast growth factor-20 (FGF-20), FGF-21, neurotrophin-3 (NT-3), growth hormone (GH), granulocyte colony stimulating factor (G-CSF), or glucocerebrosidase proteins in microorganisms that have an oxidizing environment.

BACKGROUND OF THE INVENTION

Many recently developed pharmaceuticals are therapeutic proteins. Therapeutic protein products were not routinely administered to patients until molecular biology techniques had evolved to allow production of the protein recombinantly. Therapeutic proteins are typically from a mammal, e.g., a human, and are generally produced in cultured cells derived from multicellular eukaryotic organisms, e.g., Chinese hamster ovary cells or other mammalian cells. Such mammalian cell production methods are expensive and time consuming, but are believed to allow for optimal post-translational processing of the recombinant protein. Post-translational processing includes, e.g., refolding and formation of correct disulfide bonds and glycosylation of the protein. Microorganisms are an attractive substitute for eukaryotic cells, but have not been successfully used to produce commercial scale amounts of therapeutic proteins. Microorganisms, in particular *E. coli*, do not promote post-translational processing of eukaryotic proteins. For example, many eukaryotic proteins, including many therapeutic proteins are expressed as insoluble inclusion bodies in microorganisms, including *E. coli*. Thus, there is a need for improved methods to produce active therapeutic proteins in microorganisms. The present invention solves this and other needs.

BRIEF SUMMARY OF THE INVENTION

In one aspect, the present invention provides a method of producing a soluble therapeutic protein in a microorganism that has an oxidizing environment, by a) expressing a nucleic acid that encodes the therapeutic protein in the microorganism; and then b) growing the microorganism under conditions that allow production of the soluble therapeutic protein.

Some preferred examples of therapeutic proteins for use in the invention include human fibroblast growth factor-20, human fibroblast growth factor-21, human neurotrophin-3, human growth hormone, human G-CSF, or human glucocerebrosidase.

In a first embodiment the microorganism is an *E. coli* that has an oxidizing environment. For example, the *E. coli* can be manipulated to inactivate endogenous reductase nucleic acids, e.g., a txrB gene and a gor gene. Other *E. coli* strains that can be used include, e.g., a trxB gor supp mutant strain or a trxB gshA supp mutant strain, both of which are disclosed in U.S. Pat. No. 6,872,563, which is herein incorporated by reference for all purposes. In a further embodiment the *E. coli* cells are grown at an optimal growth temperature, e.g., 37° C., and then therapeutic protein expression is induced at a temperature lower than optimal growth temperature, e.g., between 12-30° C. The microorganism can also express additional proteins to enhance solubility of the eukaryotic glycosyltransferase, e.g. a heterologous protein disulfide isomerase (PDI) or a heterologous chaperone protein, or both a heterologous PDI and a heterologous chaperone protein.

In another embodiment, the method further comprises the step of isolating the therapeutic protein. In additional embodiments, the therapeutic protein comprises a purification tag, e.g., a maltose binding protein domain or a starch binding protein domain. In additional embodiments, the soluble therapeutic protein is produced on a commercial scale. Commercial scale includes preparation of e.g., microgram, milligram, or gram scale amounts of therapeutic protein.

In another embodiment, the therapeutic protein exhibits biological or enzymatic activity after expression in a microorganism.

BRIEF DESCRIPTION OF THE DRAWINGS

FIG. 5A provides the expression and solubility of a mutant form of human growth hormone (GH) produced in trxB gor supp mutant E. coli. Nucleic acids encoding a mutant form #1 of mature human GH were cloned into Vector4, and tested for expression in DE3 trxB gor supp mutant cells. Cells bearing GH mutant #1 were sampled before (lane 3) and after (lanes 4-5) overnight induction with either 10 (lanes 4, 6) or 100 (lanes 5, 7) µM IPTG at 20° C. Induced cells were collected by centrifugation, lysed, and soluble fractions were isolated by centrifugation (lanes 6-7). A box indicates the position of human GH in the gel. The first lane is molecular weight markers, and a commercially available human GH was run as a standard in lane 2.

FIG. 5b demonstrates the expression, solubility, and purification of a second mutant form of mature human growth hormone (GH) produced in trxB gor supp mutant E. coli. Nucleic acids encoding a mutant form #2 of mature human GH were cloned into Vector4, and tested for expression in DE3 trxB gor supp mutant cells. Cells bearing GH mutant #2 were induced overnight with 10 µM IPTG at 20° C. Induced cells were collected by centrifugation, lysed, and the cell lysate was clarified first by low speed centrifugation (lane 2), followed by polyethylene imine (PEI) precipitation and higher speed centrifugation (lane 3). Human GH was captured from the PEI-clarified supernatant by passage over a HiTrap DEAE fast flow column, washed, and eluted with a NaCl gradient. Peak human GH DEAE fractions were pooled (lane 4), and applied to a ceramic hydroxyapatite (CHT) column following concentration and desalting. Human GH in the CHT flowthrough fraction (lanes 5 and 7) was further purified by size exclusion chromatography (lanes 6 and 8). Purification step samples were analyzed by SDS-PAGE and Coomassie stain (lanes 1-6) or silver stain (lanes 7-8). A box indicates the position of human GH in the gel. Molecular weight markers were run in the first lane.

DEFINITIONS

Figure 1A:
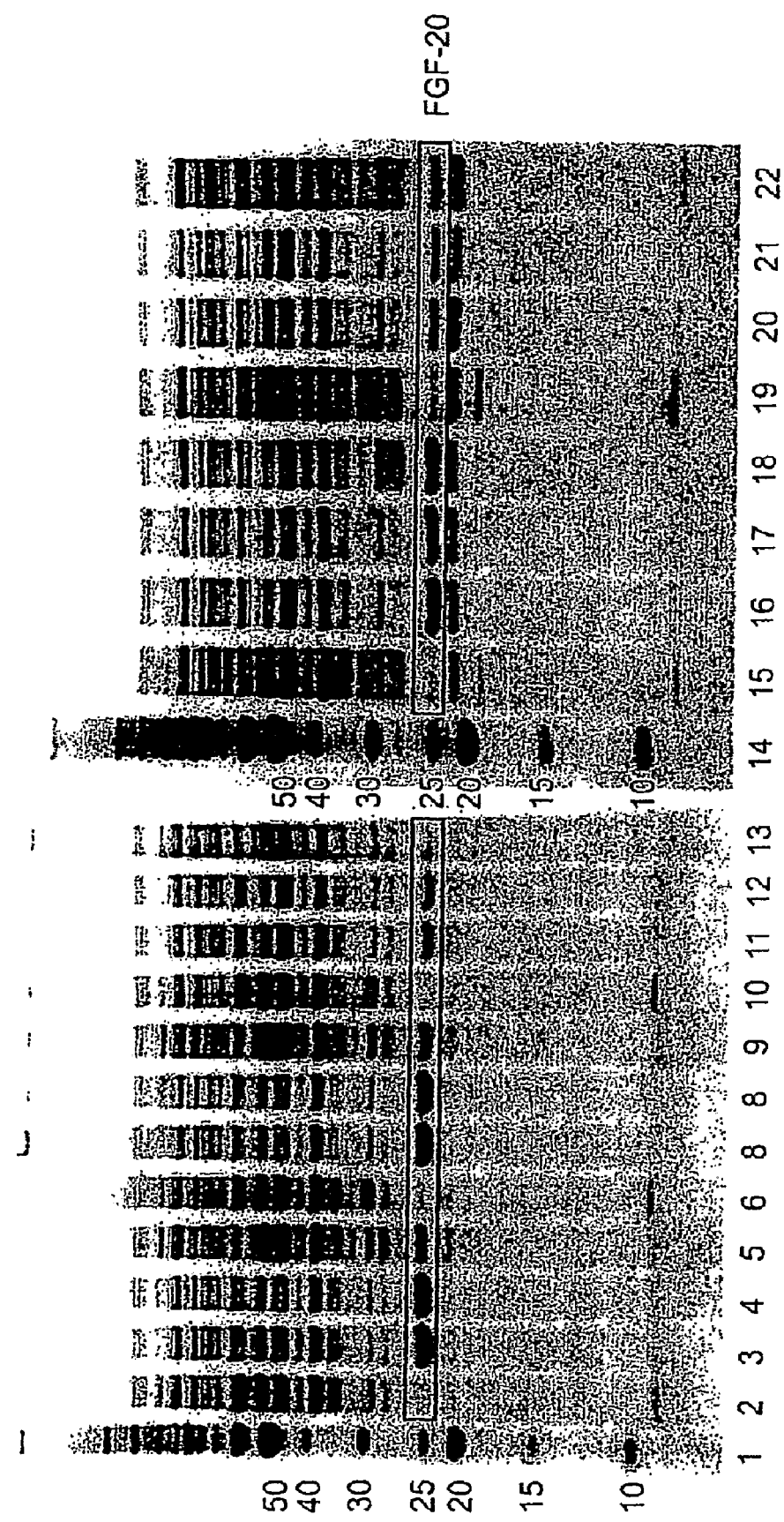
FIG. 1a demonstrates the expression of human fibroblast growth factor 20 (FGF-20) in different *E. coli* strains. Nucleic acids encoding FGF-20 were cloned into four different vector backbones: Vector1 (pCWin2, disclosed in WO 2005/067601; lanes 2, 6, 10, 15, 19), Vector2 (derived from pCWin2, truncated promoter, modified leader sequence; lanes 3, 7, 11, 16, 20), Vector3 (derived from pCWin2, modified leader sequence; lanes 4, 8, 12, 17, 21), and Vector4 (pET24a; lanes 5, 9, 13, 18, 22). Human FGF-20 expressed from these vectors was tested in the *E. coli* strains W3110 (lanes 2-4, 6-8, 10-12), BL21 DE3(lanes 5, 9, 15), a trxB gor supp mutant strain (lanes 15-17, 19-21), and a DE3 trxB gor supp mutant (lanes 18, 22). Cells were harvested after induction of protein expression for 1.5 hours (lanes 2-5) or overnight (lanes 6-13, 15-22). The cells were induced at 37° C. (lanes 2-9, 15-18) or 20° C. (lanes 10-13, 19-22). Total cell extracts were analyzed by SDS-PAGE. A box indicates the position of human FGF-20 in the gel. Molecular weight markers were run in lanes 1 and 14.

A "therapeutic protein" as used herein, refers a protein, peptide, glycoprotein or glycopeptide that is administered to a subject to treat disease or dysfunction or to improve health of the subject. In a preferred embodiment the subject is a human. In a further preferred embodiment, the therapeutic protein is a human protein. Using the methods disclosed herein, the therapeutic protein is produced in a microorganism that has an oxidizing intracellular environment. In a preferred embodiment, a therapeutic protein is one of the following: FGF-20, FGF-21, NT-3, growth hormone, G-CSF, or glucocerebrosidase. In a further preferred embodiment, a therapeutic protein is one of the following: human FGF-20, human FGF-21, human NT-3, human growth hormone, human G-CSF, or human glucocerebrosidase proteins. A soluble therapeutic protein refers to a therapeutic protein that is soluble in an aqueous solution. In some embodiments the soluble therapeutic protein is soluble in an intracellular compartment of a prokaryotic cell. All of the expressed therapeutic protein, most of the expressed therapeutic protein or some portion of the expressed therapeutic protein can be soluble in the intracellular compartment of a prokaryotic cell. In another embodiment the soluble therapeutic protein is an active protein, e.g., has enzymatic activity, or biological activity, such as binding activity to a ligand or receptor, ability to activity an intracellular signal transduction pathway, or ability to elicit an immune response in a mammal, e.g., a human. In an additional embodiment, the therapeutic protein is glycosylated or otherwise modified in vitro by one or more glycosyltransferases.

Glycosyltransferase proteins are useful for transferring a saccharide from a donor substrate to an acceptor substrate. The addition generally takes place at the non-reducing end of an oligosaccharide or carbohydrate moiety on a biomolecule. Biomolecules as defined here include, but are not limited to, biologically significant molecules such as carbohydrates, proteins (e.g., glycoproteins), and lipids (e.g., glycolipids, phospholipids, sphingolipids and gangliosides).

The following abbreviations are used herein:
Ara=arabinosyl;
Fru=fructosyl;
Fuc=fucosyl;
Gal=galactosyl;
GalNAc=N-acetylgalactosylamino;
Glc=glucosyl;
GlcNAc=N-acetylglucosylamino;
Man=mannosyl; and
NeuAc=sialyl (N-acetylneuraminyl)
FT or FucT=fucosyltransferase*
ST=sialyltransferase*
GalT=galactosyltransferase*

Arabic or Roman numerals are used interchangeably herein according to the naming convention used in the art to indicate the identity of a specific glycosyltransferase (e.g., FTVII and FT7 refer to the same fucosyltransferase).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond ($\alpha$ or $\beta$), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2, 3). Each saccharide is a pyranose or furanose.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

An "acceptor substrate" for a glycosyltransferase is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate will often vary for different types of a particular glycosyltransferase. For example, the acceptor substrate for a mammalian galactoside 2-L-fucosyltransferase ($\alpha$1,2-fucosyltransferase) will include a Gal$\beta$1,4-GlcNAc-R at a non-reducing terminus of an oligosaccharide; this fucosyltransferase attaches a fucose residue to the Gal via an $\alpha$1,2 linkage. Terminal Gal$\beta$1,4-GlcNAc-R and Gal$\beta$1,3-GlcNAc-R and sialylated analogs thereof are acceptor substrates for $\alpha$1,3 and $\alpha$1,4-fucosyltransferases, respectively. These enzymes, however, attach the fucose residue to the GlcNAc residue of the acceptor substrate. Accordingly, the term "acceptor substrate" is taken in context with the particular glycosyltransferase of interest for a particular application. Acceptor substrates for additional glycosyltransferases, are described herein. Acceptor substrates also include e.g., glycolipids, peptides, proteins, glycopeptides, glycoproteins and therapeutic proteins.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. For example, a donor substrate for fucosyltransferases is GDP-fucose. Donor substrates for sialyltransferases, for example, are activated sugar nucleotides comprising the desired sialic acid. For instance, in the case of NeuAc, the activated sugar is CMP-NeuAc. Other donor substrates include e.g., GDP mannose, UDP-galactose, GDP-N-acetylgalactosamine, CMP-NeuAc-PEG (also referred to as CMP-sialic acid-PEG), UDP-N-acetyl-glucosamine, UDP-glucose, UDP-glucorionic acid, and UDP-xylose. Sugars include, e.g., NeuAc, mannose, galactose, N-acetylgalactosamine, N-acetylglucosamine, glucose, glucorionic acid, and xylose. Bacterial, plant, and fungal systems can sometimes use other activated nucleotide sugars.

A "method of remodeling a protein, a peptide, a glycoprotein, or a glycopeptide" as used herein, refers to addition of a sugar residue to a protein, a peptide, a glycoprotein, or a glycopeptide using a glycosyltransferase. In a preferred embodiment, the sugar residue is covalently attached to a PEG molecule.

An "O-glycosylated therapeutic protein" or an "O-glycosylated soluble therapeutic protein" as used herein refer to a therapeutic protein that has been modified to include at least one sugar residue conjugated to a hydroxyl group on an amino acid of the therapeutic protein.

An "unpaired cysteine residue" as used herein, refers to a cysteine residue, which in a correctly folded protein (i.e., a protein with biological activity), does not form a disulfide bind with another cysteine residue.

A "redox couple" refers to mixtures of reduced and oxidized thiol reagents and include reduced and oxidized glutathione (GSH/GSSG), cysteine/cystine, cysteamine/cystamine, DTT/GSSG, and DTE/GSSG. (See, e.g., Clark, *Cur. Op. Biotech.* 12:202-207 (2001)).

The term "oxidant" or "oxidizing agent" refers to a compound which oxidizes molecules in its environment, i.e., which changes the molecules in its environment to become more oxidized and more oxidizing. An oxidant acts by accepting electrons, thereby becoming itself reduced after having oxidized a substrate. Thus, an oxidant is an agent which accepts electrons.

The term "oxidizing conditions" or "oxidizing environment" refers to a condition or an environment in which a substrate is more likely to become oxidized than reduced. For example, the periplasm of a wild type *E. coli* cell constitutes an oxidizing environment, whereas the cytoplasm of a wild type *E. coli* cell is a reducing environment.

An enzyme in an "oxidized state" refers to an enzyme that has fewer electrons than its reduced form.

The term "reductant" or "reducing agent" refers to a compound which reduces molecules in its environment, i.e., which changes molecules in its environment to become more reduced and more reducing. A reducing agent acts by donating electrons, thereby becoming itself oxidized after having reduced a substrate. Thus, a reducing agent is an agent which donates electrons. Examples of reducing agents include dithiothreitol (DTT), mercaptoethanol, cysteine, thioglycolate, cysteamine, glutathione, and sodium borohydride.

The term "reductase" refers to a thioredoxin reductase, glutathione or glutathione reductase (also referred to as "oxidoreductases") or any other enzyme that can reduce members of the thioredoxin or glutaredoxin systems.

The term "reductase pathways" refers to the systems in cells which maintain the environment in reducing conditions, and includes the glutaredoxin system and the thioredoxin system.

The term "reducing conditions" or "reducing environment" refers to a condition or an environment in which a substrate is more likely to become reduced than oxidized. For example, the cytoplasm of a eukaryotic cell constitutes a reducing environment.

"Disulfide bond formation" or "disulfide bond oxidation", used interchangeably herein, refers to the process of forming a covalent bond between two cysteines present in one or two polypeptides. Oxidation of disulfide bonds can be mediated by thiol-disulfide exchange between the active site cysteines of enzymes and cysteines in the target protein. Disulfide bond formation can be catalyzed by enzymes which are referred to as catalysts of disulfide bond formation or can be catalyzed by chemical means, e.g., an intracellular environment.

An enzyme in a "reduced state", has more electrons than its oxidized form.

"Disulfide bond reduction" refers to the process of cleaving a disulfide bond, thereby resulting in two thiol groups. Reduction of disulfide bonds is mediated by thiol-disulfide exchange between the active site cysteines of enzymes and cysteines in the target protein.

The term "disulfide bond isomerization" refers to an exchange of disulfide bonds between different cysteines, i.e., the shuffling of disulfide bonds. Isomerization of disulfide bonds is mediated by thiol-disulfide exchange between the active site cysteines of enzymes and cysteines in the target protein and catalyzed by isomerases. In *E. coli*, isomerization is catalyzed by DsbC or DsbG a periplasmic disulfide bond oxidoreductase.

A "catalyst of disulfide bond formation" is an agent which stimulates disulfide bond formation. Such an agent must be in an oxidized state to be active.

A "catalyst of disulfide bond isomerization", also referred to as an "disulfide bond isomerase" is an agent which stimulates disulfide bond isomerization. Such an agent must be in a reduced form to be active.

The term "contacting" is used herein interchangeably with the following: combined with, added to, mixed with, passed over, incubated with, flowed over, etc.

"Chaperone proteins" are proteins that are known to promote proper folding of newly synthesized proteins. Chaperone proteins include, e.g., trigger factor; members of the Hsp70 chaperone family, e.g. DnaK; members of the Hsp 100 chaperone family, e.g. ClpB, and members of the Hsp60 chaperone family, e.g. GroEL. See, e.g., Sorensen and Mortensen, *Microbial Cell Factories*, 4: (2005). Chaperones are also known that allow protein folding at 4° C., e.g., Cpn60 and Cpn10 from *Oleispira antartica* RB8$^T$. See, e.g., Id. and Ferrer et al., *Nat. Biotechnol.* 21:1266-1267 (2003).

"Protein disulfide isomerases" or "PDI proteins" can make or shuffle disulfide bonds. PDI proteins are described e.g., in Georgiou et al. U.S. Pat. No. 6,027,888, which is herein incorporated by reference for all purposes. PDI proteins are derived from eukaryotic and prokaryotic organisms. Eukaryotic PDI proteins include those of the Interpro family IPR005792 Protein disulphide isomerase. Exemplary eukaryotic PDI proteins include PDI proteins from e.g., rat liver PDI (SEQ ID NO:14), Erolp (SEQ ID NO:15) and Pdilp (SEQ ID NO:16) proteins from *Sacchromyces*. Prokaryotic proteins include e.g., DsbC from *E. coli*. See, e.g., Frand et al., *Trends in Cell Biol.* 10:203-210 (2000).

Other prokaryotic proteins that act to maintain the redox state of protein disulfide bonds include, e.g., DsbB (SEQ ID NO:17), DsbA (SEQ ID NO:18), DsbC (SEQ ID NO:19), DsbD (SEQ ID NO:20), and DsbG (SEQ ID NO:21) from *E. coli*. These proteins are well known in the art and are described in, e.g., Beckwith et al. U.S. Pat. No. 6,872,563, which is herein incorporated by reference for all purposes.

Any of the PDI proteins or chaperonin proteins listed herein can be expressed in a microorganism with a therapeutic protein to enhance solubility of the therapeutic protein.

The term "PEG" refers to poly(ethylene glycol). PEG is an exemplary polymer that has been conjugated to peptides. The use of PEG to derivatize peptide therapeutics has been demonstrated to reduce the immunogenicity of the peptides and prolong the clearance time from the circulation. For example, U.S. Pat. No. 4,179,337 (Davis et al.) concerns non-immunogenic peptides, such as enzymes and peptide hormones coupled to polyethylene glycol (PEG) or polypropylene glycol. Between 10 and 100 moles of polymer are used per mole peptide and at least 15% of the physiological activity is maintained.

The term "specific activity" as used herein refers to the catalytic activity of an enzyme, e.g., a recombinant glycosyltransferase of the present invention, and may be expressed in activity units. As used herein, one activity unit catalyzes the formation of 1 µmol of product per minute at a given temperature (e.g., at 37° C.) and pH value (e.g., at pH 7.5). Thus, 10 units of an enzyme is a catalytic amount of that enzyme where 10 µmol of substrate are converted to 10 µmol of product in one minute at a temperature of, e.g., 37° C. and a pH value of, e.g., 7.5.

"N-linked" oligosaccharides are those oligosaccharides that are linked to a peptide backbone through asparagine, by way of an asparagine-N-acetylglucosamine linkage. N-linked oligosaccharides are also called "N-glycans." Naturally occurring N-linked oligosaccharides have a common pentasaccharide core of $Man_3GlcNAc_2$. They differ in the presence of, and in the number of branches (also called antennae) of peripheral sugars such as N-acetylglucosamine, galactose, N-acetylgalactosamine, fucose and sialic acid. Optionally, this structure may also contain a core fucose molecule and/or a xylose molecule. Using recombinant glycosyltransferases, oligosaccharides can be produced that mimic natural N-linked structures or that are designed by the user. Glycosyltransferases that generate N-linked oligosaccharides include, e.g., GnT1, GalT1, and ST3Gal3 enzymes.

"O-linked" oligosaccharides are those oligosaccharides that are linked to a peptide backbone through threonine, serine, hydroxyproline, tyrosine, or other hydroxy-containing amino acids. Using the soluble eukaryotic glycosyltransferases, oligosaccharides can be produced that mimic natural O-linked structures or that are designed by the user.

A "substantially uniform glycoform" or a "substantially uniform glycosylation pattern," when referring to a glycoprotein species, refers to the percentage of acceptor substrates that are glycosylated by the glycosyltransferase of interest (e.g., fucosyltransferase). It will be understood by one of skill in the art, that the starting material may contain glycosylated acceptor substrates. Thus, the calculated amount of glycosylation will include acceptor substrates that are glycosylated by the methods of the invention, as well as those acceptor substrates already glycosylated in the starting material.

The term "biological activity" typically refers to an enzymatic activity of a protein. For example, biological activity of a sialyltransferase refers to the activity of transferring a sialic acid moiety from a donor molecule to an acceptor molecule. Other biological activities include ligand binding by e.g., a hormone or receptor, induction of a second messenger system by e.g., a cytokine, receptor binding by e.g., a ligand, and ability to elicit an immune response.

"Commercial scale" refers to gram scale production of a therapeutic protein in a single reaction. In preferred embodiments, commercial scale refers to production of at least about 0.2, 0.5, 1, 2, 5, 10, 15, 25, 50, 75, 80, 90 or 100, 125, 150, 175, 200, 500 or 1000 grams of a therapeutic protein in a single reaction. In preferred embodiments, commercial scale refers to production of between 1 U/kg protein to 1000 U/Kg protein of soluble, active therapeutic protein.

The term "substantially" in the above definitions of "substantially uniform" generally means at least about 60%, at least about 70%, at least about 80%, or more preferably at least about 90%, and still more preferably at least about 95% of the acceptor substrates on a therapeutic protein are glycosylated.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Protein", "polypeptide", or "peptide" refer to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and reintroduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant protein" is one which has been produced by a recombinant cell. In preferred embodiments, a recombinant eukaryotic glycosyltransferase is produced by a recombinant bacterial cell.

A "fusion protein" refers to a protein comprising amino acid sequences that are in addition to, in place of, less than, and/or different from the amino acid sequences encoding the original or native full-length protein or subsequences thereof. More than one additional domain can be added to a glycosyltransferase as described herein, e.g., an accessory domain and an epitope tag or purification tag, or multiple epitope tags or purification tags.

Components of fusion proteins include "accessory enzymes" and/or "purification tags." An "accessory enzyme" as referred to herein, is an enzyme that is involved in catalyzing a reaction that, for example, forms a substrate for a glycosyltransferase. An accessory enzyme can, for example, catalyze the formation of a nucleotide sugar that is used as a donor moiety by a glycosyltransferase. An accessory enzyme can also be one that is used in the generation of a nucleotide triphosphate required for formation of a nucleotide sugar, or in the generation of the sugar which is incorporated into the nucleotide sugar.

The recombinant therapeutic proteins of the invention can be constructed and expressed as a fusion protein with a molecular "purification tag" at one end, which facilitates purification of the protein. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAsp AspLys (SEQ ID NO:22) or a substantially identical variant thereof. Other epitope tags that can be used in the invention include, e.g., myc tag, AU1, AU5, DDDDK (EC5) (SEQ ID NO:23), E tag, E2 tag, Glu-Glu, a 6 residue peptide, EYMPME (SEQ ID NO:24), derived from the Polyoma middle T protein, HA, HSV, IRS, KT3, S tage, S1 tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

Other suitable tags are known to those of skill in the art, and include, for example, an affinity tag such as a hexahistidine peptide or other poly-histidine peptides, which will bind to metal ions such as nickel or cobalt ions. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, E. coli thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Starch binding domains, such as a maltose binding domain from E. coli and SBD (starch binding domain) from an amylase of A. niger, are described in WO 99/15636, herein incorporated by reference. Affinity purification of a fusion protein comprising a starch binding domain using a betacycloctextrin (BCD)-derivatized resin is described in U.S. Ser. No. 60/468, 374, filed May 5, 2003, herein incorporated by reference in its entirety.

Therapeutic proteins can also include a self-cleaving protein tag, such as an "intein". Inteins facilitate removal of, e.g., a purification or epitope tag. Inteins and kits for their use are commercially available, e.g., from New England Biolabs.

The term "functional domain" with reference to glycosyltransferases, refers to a domain of the glycosyltransferase that confers or modulates an activity of the enzyme, e.g., acceptor substrate specificity, catalytic activity, binding affinity, localization within the Golgi apparatus, anchoring to a cell membrane, or other biological or biochemical activity. Examples of functional domains of glycosyltransferases include, but are not limited to, the catalytic domain, stem region, and signal-anchor domain.

The terms "expression level" or "level of expression" with reference to a protein refers to the amount of a protein produced by a cell. The amount of protein produced by a cell can be measured by the assays and activity units described herein or known to one skilled in the art. One skilled in the art would know how to measure and describe the amount of protein produced by a cell using a variety of assays and units, respectively. Thus, the quantitation and quantitative description of the level of expression of a protein, e.g., a glycosyltransferase, is not limited to the assays used to measure the activity or the units used to describe the activity, respectively. The amount of protein produced by a cell can be determined by standard known assays, for example, the protein assay by Bradford (1976), the bicinchoninic acid protein assay kit from Pierce (Rockford, Ill.), or as described in U.S. Pat. No. 5,641,668. Another method of determining protein expression is to analyze a lysate or other sample containing the protein using gel electrophoresis, e.g., SDS-PAGE, followed by a visualization step. Visualization steps include protein dyes and stains, e.g., Coomassie or silver stain, or inmunoassays, such as Western blot analysis using an antibody that will specifically bind to the protein of interest. Antibodies can be directed against the glycosyltransferase or against a purification or epitope tag covalently bound to the protein.

The term "enzymatic activity" refers to an activity of an enzyme and may be measured by the assays and units described herein or known to one skilled in the art. Examples of an activity of a glycosyltransferase include, but are not limited to, those associated with the functional domains of the enzyme, e.g., acceptor substrate specificity, catalytic activity, binding attinity, localization within the Golgi apparatus, anchoring to a cell membrane, or other biological or biochemical activity.

A "subsequence" refers to a sequence of nucleic acids or amino acids that comprise a part of a longer sequence of nucleic acids or amino acids (e.g., protein) respectively.

The term "nucleic acid" refers to a deoxyribonucleotide or ribonucleotide polymer in either single-or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette. In preferred embodiments, a recombinant expression cassette encoding an amino acid sequence comprising a eukaryotic glycosyltransferase is expressed in a bacterial host cell.

A "heterologous sequence" or a "heterologous nucleic acid", as used herein, is one that originates from a source foreign to the particular host cell, or, if from the same source, is modified from its original form. Thus, a heterologous glycoprotein gene in a eukaryotic host cell includes a glycoprotein-encoding gene that is endogenous to the particular host cell that has been modified. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

The term "isolated" refers to material that is substantially or essentially free from components which interfere with the activity of an enzyme. For a saccharide, protein, or nucleic acid or the invention, the term "isolated" refers to material that is substantially or essentially free from components which normally accompany the material as found in its native state. Typically, an isolated saccharide, protein, or nucleic acid of the invention is at least about 80% pure, usually at least about 90%, and preferably at least about 95% pure as measured by band intensity on a silver stained gel or other method for determining purity. Purity or homogeneity can be indicated by a number of means well known in the art. For example, a protein or nucleic acid in a sample can be resolved by polyacrylamide gel electrophoresis, and then the protein or nucleic acid can be visualized by staining. For certain purposes high resolution of the protein or nucleic acid may be desirable and HPLC or a similar means for purification, for example, may be utilized.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The terms "identical" or percent "identity," in the context of two or more nucleic acids or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or proteins, refers to two or more sequences or subsequences that have at least greater than about 60% nucleic acid or amino acid sequence identity, 65%, 70%, 75%, 80%, 85%, 90%, preferably 91%, 92%, 93%, 94%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is typically at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32-48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given protein. For instance, the codons CGU, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every polynucleotide sequence described herein which encodes a protein also describes every possible silent variation, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid which encodes a protein is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

One of skill will appreciate that many conservative variations of proteins, e.g., therapeutic proteins, and nucleic acid which encode proteins yield essentially identical products. For example, due to the degeneracy of the genetic code, "silent substitutions" (i.e., substitutions of a nucleic acid sequence which do not result in an alteration in an encoded protein) are an implied feature of every nucleic acid sequence which encodes an amino acid. As described herein, sequences are preferably optimized for expression in a particular host cell used to produce the chimeric glycosyltransferases (e.g., yeast, human, and the like). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations".

The practice of this invention can involve the construction of recombinant nucleic acids and the expression of genes in host cells, preferably bacterial host cells. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (1999 Supplement) (Ausubel). Suitable host cells for expression of the recombinant polypeptides are known to those of skill in the art, and include, for example, prokaryotic cells, such as *E. coli*.

Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis);

Arnheim & Levinson (Oct. 1, 1990) C&EN 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077-1080; Van Brunt (1990) *Biotechnology* 8: 291-294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039.

DETAILED DESCRIPTION OF THE INVENTION

I. Introduction

This invention provides for the first time, methods of enhancing production of soluble, active therapeutic proteins in microorganisms by producing the therapeutic proteins in microorganisms that have oxidizing intracellular environments. In preferred embodiments, the therapeutic proteins typically are inactive, insoluble, or expressed at very low levels in microorganisms that have a reducing environment, e.g., wild type *E. coli*. The invention encompasses use of microorganisms that have oxidizing intracellular environments naturally, such as *Pseudomonas*. The invention also encompasses use of microorganisms that have reducing intracellular environments naturally, but that are manipulated to have an oxidizing intracellular environment.

Wild type *E. coli* is an example of a microorganism that naturally has a reducing intracellular environment. Expression of many heterologous proteins in *E. coli* frequently can be difficult or impractical because disulfide bonds are not properly oxidized, leading to protein misfolding and expression of proteins in inclusion bodies. *E. coli* and other organisms that have a naturally reducing intracellular environment can be manipulated, however, to generate an intracellular environment that favors oxidation of disulfide bonds. For example, *E. coli* can be manipulated to reduce activity of endogenous reductase proteins either by mutation of the nucleic acids encoding those proteins or by manipulation of other protein activities in an intracellular oxidation-reduction cycle. Also in *E. coli*, inactivating mutations in the thioredoxin reductase protein (trxB), the glutathione reductase protein (gor), or in both proteins result in cells that have an oxidizing environment. *E. coli* cells that have mutations in trxB and gor are commercially available, e.g., from Novagen.

In one embodiment, production of soluble, active therapeutic proteins in microorganisms that have oxidizing intracellular environments is further enhanced by growing the cells under conditions that reduce the level of recombinant protein production, i.e., the therapeutic protein, below that of a maximal level.

II. Expression of Soluble, Active Therapeutic Proteins in Microorganisms

Any therapeutic protein that is predominantly insoluble when expressed in a reducing environment, e.g., wild type *E. coli*, can be expressed in a microorganism that has an intracellular oxidizing environment to facilitate expression of an active, soluble protein. Once soluble therapeutic proteins are produced, they can be post-translationally modified in vitro through the action of e.g., glycosyltransferases.

Microorganisms that have an oxidative, intracellular environment can be used to generate most proteins and can be used to enhance protein expression, particularly as compared to proteins that are expressed in inclusion bodies in, e.g., wild type *E. coli*.

Preferred therapeutic proteins for production using microorganisms that have an oxidative, intracellular environment, include e.g., FGF-20, FGF-21, neurotrophin 3, growth hormone, G-CSF, and glucocerebrosidase. These proteins can be expressed as a mature, fully processed form or as an unprocessed or partially processed form, e.g., comprising a pro sequence or secretion sequence. The therapeutic proteins can be further modified to e.g., include glycosylation sites or increase resistance to proteases. Examples of, e.g., human FGF-20, human FGF-21, G-CSF, and human growth hormone and other mutants are disclosed in e.g., WO 2004/103275, WO 2005/055946, WO 2005/070138, International application PCT/US05/039226, filed Oct. 31, 2005, and published as WO06/050247; International application PCT/US06/013903, filed Apr. 10, 2006; and U.S. Provisional Application No. 60/832,461, filed Jul. 21, 2006; each of which is herein incorporated by reference for all purposes. Any of these mutant proteins can be expressed using the methods disclosed herein.

After expression of the soluble therapeutic protein using the methods of the invention, the soluble therapeutic protein will preferably be an active protein. Those of skill will recognize how to determine the activity of a particular therapeutic protein. For example, hormones or growth factors can be assayed for binding to an appropriate receptor or for an appropriate response in a cell based or animal model. Receptor proteins can be assayed for binding to an appropriate ligand or for an appropriate response in a cell based or animal model. Enzymatic assays of enzymes or enzymatic inhibitors can be performed to determine activity. Cytokines can be assayed for activity using an appropriate cell based model or animal model. Therapeutic proteins that are vaccines, can be assayed for an ability to elicit an immune response in a model animal or in a human.

In one embodiment, a soluble, active therapeutic protein made by the methods described herein, e.g., FGF-20, FGF-21, neurotrophin 3, growth hormone, G-CSF, and glucocerebrosidase; has enzymatic or biological activity levels, e.g., U/cell or U/mg protein, up to 1.1, 1.2, 1.5, 2, 3, 5, 10, 15, 20, 50, 100, 500, 1000, or up to 10,000 times greater than activity levels of the same therapeutic protein expressed in a microorganism with a reducing environment.

In one embodiment, a soluble, active therapeutic protein made by the methods described herein, FGF-20, FGF-21, neurotrophin 3, growth hormone, G-CSF, and glucocerebrosidase; has improved therapeutic properties, up to 1.1, 1.2, 1.5, 2, 3, 5, 10, 15, 20, 50, 100, 500, 1000, or up to 10,000 times greater than those of the same therapeutic protein expressed in a microorganism with a reducing environment.

Enhancement of production of soluble, active therapeutic proteins in microorganisms that have oxidizing intracellular environments as compared to production in microorganisms that have reducing intracellular environments is demonstrated in Example 1.

III. Intracellular, Oxidizing Environments

In preferred embodiments, soluble, active therapeutic proteins are expressed in microorganisms that have oxidizing intracellular environments.

A. Prokaryotic Microorganisms that have Oxidizing Intracellular Environments The method of the invention are carried out using prokaryotic microorganisms that have oxidizing intracellular environments. Such microorganisms include prokaryotic microorganisms that have endogenous, intracellular oxidizing environments and prokaryotic microorganisms that are genetically manipulated to have an intracellular oxidizing environment.

Some prokaryotic organisms have endogenous, intracellular oxidizing environments and, thus, promote formation of protein disulfide bonds inside the cell. Oxidizing intracellular compartments in prokaryotic organisms specifically exclude a bacterial periplasmic space. Prokaryotic organisms that have endogenous, intracellular oxidizing environments can be used in to produce soluble, active eukaryotic glycosyltransferases in an intracellular compartment. Prokaryotic organisms with endogenous, intracellular oxidizing environments include members of e.g., *Pseudomonas* species, including *testosteroni putida, aeruginosa, syringae*, and *fluorescens*; some gram positive bacteria; and some gram negative bacteria. Additional *Pseudomonas* species and strains are described in, e.g., U.S. Patent Application Publication No. US 2005/0186666, published Aug. 25, 2005, which is herein incorporated by reference for all purposes. Gram positive bacteria include, e.g., *Bacillus, Listeria, Staphylococcus, Streptococcus, Enterococcus*, and *Clostridium* species.

Prokaryotic organisms with modification of a redox pathway can also be used in the methods of the invention to produce soluble, active eukaryotic glycosyltransferases or soluble, active therapeutic proteins. Modifications can be performed on prokaryotic organisms that have a reducing environment, e.g., *E. coli* or other gram negative bacteria or some gram positive bacteria. The prokaryotic microorganisms are modified to promote an oxidizing intracellular environment, thereby enhancing intracellular disulfide bond formation and protein refolding of e.g., therapeutic proteins and eukaryotic glycosyltransferases.

Many prokaryotic organisms use two pathways to reduce disulfide bonds that form in some cytoplasmic proteins, including recombinantly expressed proteins. The components of these pathways can be manipulated to promote formation of an intracellular oxidizing environment. The first pathway is the thioredoxin system, which generally includes a thioredoxin reductase and thioredoxin. Thioredoxin reductase maintains thioredoxin in a reduced state. The second pathway is the glutaredoxin system, which generally includes a glutathione oxidoreductase, glutathione, and glutaredoxins. Inactivating mutations of some components of these redox pathways can ultimately increase the formation of disulfide bonds in expressed proteins, and in the case of heterologous proteins expressed in the prokaryotic organism, can increase the solubility and activity of the expressed heterologous proteins. For example, in *E. coli* elimination of thioredoxin reductase activity results in an accumulation of oxidized thioredoxin that act as an oxidase in the intracellular compartment.

Some preferred examples are prokaryotic microorganisms that have reduced or absent reductase activity. For example, the activity of a thioredoxin reductase and/or a glutathione oxidoreductase can be reduced or eliminated to modify the intracellular environment, thereby producing an oxidizing intracellular environment that favors formation of disulfide bonds.

For example, *E. coli* strains that have mutations in both the thioredoxin reductase gene (trxB) and the glutathione oxidoreductase gene (gor) are able to express proteins with higher levels of disulfide bond formation. See, e.g., Prinz et al., *J. Biol Chem.* 272:15661-15667 (1997). These trxB gor double mutants grow very slowly on most growth media, although growth can be enhanced by addition of a reductant, such as DTT. However, the double mutant strains frequently give rise to suppressor mutant strains that retain the trxB gor mutations and that grow faster in medium lacking DTT. One example of a trxB gor suppressor mutation in *E. coli* is a mutation of the gene ahpC, which encodes a catalytic subunit of the alkyl hydroperoxidase, AhpCF. This suppressor mutation adds a triplet to the DNA that encodes the catalytic site of the AhpCF enzyme. Fast growing double mutant *E. coli* strains, e.g., trxB, gor, supp and trxB, gshA, supp strains are disclosed in e.g., U.S. Pat. No. 6,872,563, which is herein incorporated by reference for all purposes. Such manipulated *E. coli* strains, e.g., trxB, gor, supp strains, are commercially available, e.g., under the trade names ORIGAMI™, ORIGAMI 2™, and ROSETTA-GAMI™, from e.g., EMD Biosciences, Inc. Other *E. coli* mutations can result in an oxidizing intracellular environment, e.g., trxB, gshA and trxB, gshA supp strains.

Other manipulations of components of a redox pathway in a microorganism can be used to enhance formation of disulfide bonds in a protein, e.g., a therapeutic protein and a heterologous glycosyltransferase. For example, proteins with oxidizing activity, e.g., *E. coli* thioredoxin proteins in trxB, gor mutant strains, can be overexpressed in the prokaryotic microorganism. Another example is expression or overexpression of thioredoxin mutants that have enhanced oxidizing activity. Examples of such mutants are described in, e.g., Bessette, et al. *PNAS* 96:13703-13708 (1999). Targeted cytoplasmic expression of certain oxidizing enzymes can also be used to enhance formation of intracellular disulfide bonds. For example oxidizing proteins that are typically expressed in the periplasmic space, e.g., DsbC, can be expressed in a bacterial cytoplasm by e.g., deleting a periplasmic targeting sequence or including a cytoplasmic retention sequence. Other oxidizing periplasmic proteins can be expressed in the bacterial cytoplasm to enhance oxidation of cytoplasmic proteins, e.g., by deleting a periplasmic targeting sequence or including a cytoplasmic retention sequence.

Thioredoxin reductase nucleic acids, glutathione oxidoreductase nucleic acids, thioredoxin nucleic acids, glutathione nucleic acids, and nucleic acids encoding other proteins involved in maintenance of an intracellular redox environment can be identified in other bacteria, e.g., *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. Such genes can be identified by sequence analysis and comparison to known thioredoxin reductase genes, glutathione oxidoreductase genes, and genes encoding other proteins involved in maintenance of an intracellular redox environment or to the amino acid sequence of the encoded products. The encoded proteins can be further identified functionally by enzymatic assays or by genetic complementation assays of *E. coli* mutants of an appropriate gene function. The endogenous thioredoxin reductase and glutathione oxidoreductase genes can be e.g., mutated to inactivate the gene product using standard molecular biology techniques and those mutated strains can also be used to express proteins with increased levels of disulfide bond formation, as compared to unmutated strains.

B. Identification of Intracellular, Oxidizing Environments

Protein refolding and protein activity frequently depend on the correct formation of disulfide bonds. Disulfide bonds are reversible thiol-disulfide (SH-SS) exchange reactions that are greatly influenced by the redox state of the environment surrounding the protein. In many cells, including *E. coli* and other prokaryotic organisms, glutathione, a tripeptide containing cysteine, is an important thiol-disulfide redox buffer. The redox state of prokaryotic microorganisms is also affected by other proteins, such as thioredoxins. Reductase proteins, in turn, regulate the redox state of glutathione, glutaredoxins and thioredoxins. In *E. coli* glutathiones, encoded by gshA and gshB, regulates the redox state of glutaredoxins. Reductase proteins include, e.g., thioredoxin reductase and glutathione oxidoreductase. *E. coli* has thioredoxins encoded by trxA and trxC genes, glutaredoxin 1, glutaredoxin 2, and glutaredoxin 3, encoded by grxA, grxB, and grxC genes. Many of the proteins that regulate the oxidation state of a cell, e.g., thioredoxin, glutathione, thioredoxin reductase and glutathione oxidoreductase, comprise an active site $CX_1X_2C$ motif. The proteins also comprise a protein structural motif known as the thioredxoin fold.

One method to identify prokaryotes that have an oxidizing intracellular environment is to measure the ratio of reduced glutathione (GSH) to oxidized glutathione (GSSG). Optimum ratios of GSH/GSSG for protein folding have been determined. In vitro, maximum yields of properly folded protein occur at GSH/GSSG ratios of less than 50, preferably less than 40, more preferably less than 30, still more preferably less than 20, and most preferably less than 10. In mammalian cells, cytoplasmic GSH/GSSG ratios ranged from 30/1 to 100/1, while secretory pathway (where most protein refolding occurs) GSH/GSSG ratios ranged from 1/1 to 3/1. Hwang et al., *Science* 257:1496-1502 (1992). *E. coli* express very few intracellular proteins with disulfide bonds. *E. coli* proteins that have disulfide bonds are secreted into the periplasmic space, which has an oxidizing environment. Typical wild type intracellular *E. coli* GSH/GSSG ratios ranged from 50/1 to 200/1. Hwang et al. supra.

The methods of the invention can by used to produce soluble eukaryotic glycosyltransferases in prokaryotic organisms that have an oxidizing intracellular environment. Microorganisms with an oxidizing intracellular environment typically have GSH/GSSG ratios of less than 50, preferably less than 40, more preferably less than 30, still more preferably less than 20, and most preferably less than 10. Thus, in some embodiments, the microorganisms of the invention will have GSH/GSSG ratios that range, e.g., from 0 to 50, or from 0.1 to 25, or from 0.5 to 10.

Prokaryotic organisms with intracellular environments can be identified by e.g., determining the intracellular GSH/GSSG ratio of the prokaryotic organisms. Assays for total glutathione concentration are commercially available from, e.g., Sigma. Assays for determination of a GSH/GSSG ratio are described, e.g., in Hwang et al., *Science* 257:1496-1502 (1992). Methods to quantify intracellular content of GSH and GSSG by derivitization with N-(1-pyrenyl)maleimide (NPM) followed by quantification using HPLC are described in Ostergaard, et al., *J. Cell Biol.* 166:337-345 (2004).

A number of additional assays are available to those of skill to determine whether a prokaryotic organism has an intracellular, oxidizing environment. Those assays include measurement of glutathione reductase activity and glutathione pool redox state (Tuggle and Fuchs, *J. Bacter.* 162:448-450 (1985)), sensitivity to thiol-specific oxidants in growth medium (Prinz et al., *J. Biol. Chem.* 272:15661-15667 (1997)), transcriptional activation of the OxyR gene in *E. coli* after exposure to hydrogen peroxide or diamide (Bessette et al., *PNAS* 96:13703-13708 (1999), measurement of the redox state of a reporter gene, such as a redox sensitive green fluorescent protein, (rxYFP) (Ostergaard et al., *J. Cell Biol.* 166: 337-345 (2004)), detection of glutathione using glutathione sensitive dyes such as monochlorobimane, CellTracker Green CMFDA, o-phthaldialdehyde, and naphthalene-2,3-dicaboxaldehyde from e.g., Molecular Probes, and oxidation of cysteine residue in proteins after exposure of cells to a sulfhydryl-alkylating reagent, such as 4-acetamido-4'-maleimidystibene-2,2-disulfonic acid (Jurado et al., *J. Mol. Biol.* 320:1-10 (2002)).

IV. Enhancement of Soluble Therapeutic Protein Expression

Reduction of disulfide bonds in heterologously expressed proteins, such as the therapeutic proteins used in the methods of the invention, frequently results in protein misfolding and precipitation out of solution. In bacterial cells such as e.g., *E. coli*, misfolded proteins are expressed as insoluble inclusion bodies. Solubilization of a protein is generally indicated by the presence of the protein in an aqueous fraction after centrifugation at an appropriate speed for an appropriate period. In addition, expression of properly folded proteins results in increased levels of protein activity. Thus, assays of enzyme activity can also be used to determine whether proper protein folding has occurred.

Expression of a solubilized therapeutic protein in a microorganism with an oxidizing environment can be compared to expression of a solubilized therapeutic protein in a microorganism with a reducing environment, e.g., wild type *E. coli*. In some embodiments, a therapeutic protein expressed in a microorganism with an oxidizing environment in a soluble fraction at levels that are up to 1.1, 1.2, 1.5, 2, 3, 5, 10, 15, 20, 50, 100, 500, 1000, or up to 10,000 times greater than soluble levels of the same therapeutic protein when expressed in a microorganism with a reducing environment. Expression of soluble therapeutic proteins can also be determined by protein activity. Thus, a therapeutic protein expressed in a soluble fraction of microorganism with an oxidizing environment can have activity levels, e.g., U/cell or U/mg protein, up to 1.1, 1.2, 1.5, 2, 3, 5, 10, 15, 20, 50, 100, 500, 1000, or up to 10,000 times greater than activity levels of the same therapeutic protein expressed in a soluble fraction of a microorganism with a reducing environment.

A. Determination of Protein Solubility

Solubility of therapeutic proteins can be determined as disclosed above, by determining protein levels in an aqueous fraction after centrifugation at an appropriate speed for an appropriate period. Protein levels can be determined using methods known to those of skill in the art, e.g., immunoassays or direct comparison of proteins separated by, e.g., SDS-PAGE. Immunoassays can be performed using antibodies specific for the therapeutic protein of interest or using antibodies specific for an epitope or purification tag that is covalently linked to the therapeutic protein.

Solubility can also be determined by assaying an appropriate enzymatic activity of the therapeutic proteins in, e.g., a soluble fraction of a cell lysate.

Enzyme amounts or concentrations are expressed in activity units, which is a measure of the initial rate of catalysis. One activity unit catalyzes the formation of 1 µmol of product per minute at a given temperature (typically 37° C.) and pH value (typically 7.5). Thus, 10 units of an enzyme is a catalytic amount of that enzyme where 10 µmol of substrate are converted to 10 µmol of product in one minute at a temperature of 37° C. and a pH value of 7.5.

The reaction mixture may include monovalent or divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

B. Further Enhancement of Soluble Protein Expression

Further enhancement of solubility of therapeutic proteins can occur, e.g., by reducing the rate of protein expression in a cell or by expressing the protein in combination with, e.g. a chaperone protein.

Enhancing the rate of formation of appropriate disulfide bonds can lead to higher expression of active, soluble therapeutic proteins. Another method to enhance expression of active, soluble therapeutic proteins is to reduce the rate of protein expression thereby allowing the nascent polypeptide more time to achieve a stable, soluble conformation. The combination of the two methods, as described herein, is a preferred embodiment of the invention. Maximal expression of a heterologous protein generally occurs under optimal growth condition for the host cells. One method to slow the expression of proteins is to slow the growth rate of the cells. In a preferred embodiment, host cells are grown at a temperature below the optimal growth temperature. Those of skill can easily determine an optimal growth temperature for any particular microorganism.

The temperature used to slow protein production will depend on the optimal growth temperature of the host cells. As an example, E. coli and many other bacteria have an optimal growth temperature of 37° C. Thus, a temperature lower than an optimal growth temperature for E. coli or for other bacteria that grow optimally at 37° C. could be between 4-35° C., between 12-30° C., or between 15-20° C. In a preferred embodiment the temperature lower than an optimal growth temperature for E. coli or for other bacteria that grow optimally at 37° C. is between 18 and 23° C. For cells that grow optimally at 30° C., as do many yeasts, a temperature lower than an optimal growth temperature could be between 10 and 25° C., between 12 and 21° C., or between 15 and 20° C.

Another method to reduce the rate of expression of a heterologous protein is to vary the concentration of a molecule that regulates expression from an inducible promoter. For example, some lacY mutations allow protein expression to be controlled by varying the amount of IPTG, the inducer molecule, in the medium.

In some embodiments, a therapeutic protein is expressed in a microorganism that has an oxidizing environment and that further comprises a heterologous chaperone protein. Chaperone proteins include, e.g., trigger factor; members of the Hsp70 chaperone family, e.g. DnaK; members of the Hsp100 chaperone family, e.g. ClpB, and members of the Hsp60 chaperone family, e.g. GroEL. See, e.g., Sorensen and Mortensen, *Microbial Cell Factories*, 4: 1 (2005) Chaperones are also known that allow protein folding at 4° C., e.g., Cpn60 and Cpn10 from *Oleispira antartica* RB8$^T$. See, e.g., Id. and Ferrer et al., *Nat. Biotechnol.* 21:1266-1267 (2003). Exemplary chaperonin proteins include, but are not limited to, those listed in the attached informal sequence listing.

In other embodiments, a therapeutic protein is expressed in a microorganism that has an oxidizing environment that further comprises a heterologous protein disulfide isomerase (PDI). PDI proteins can make or shuffle disulfide bonds. PDI proteins are described e.g., in Georgiou et al. U.S. Pat. No. 6,027,888, which is herein incorporated by reference for all purposes. PDI proteins include e.g., rat liver PDI, Ero1p and Pdi1p proteins from *Sacchromyces*, and DsbB, DsbA, DsbC, and DsbC from *E. coli*. See, e.g., Frand et al., *Trends in Cell Biol.* 10:203-210 (2000). Exemplary PDI proteins include, but are not limited to, those listed in the attached informal sequence listing.

In a further embodiment, a therapeutic protein is expressed in a microorganism that has an oxidizing environment and that also comprises a heterologous chaperone protein and a heterologous PDI protein.

V. Expression of Soluble, Active Therapeutic Proteins in Microorganisms that have Oxidizing Environments Soluble, active therapeutic proteins of the invention can be expressed in a variety of microorganisms with oxidizing intracellular environments, including E. coli, and other bacterial hosts, as described above.

Typically, the polynucleotide that encodes the therapeutic protein is placed under the control of a promoter that is functional in the desired microorganism that has an oxidizing environment. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired microorganism that has an oxidizing environment.

Examples of expression vectors include, e.g., the pCWin1 vector and pCWin2 vector, both disclosed in WO 2005/067601, which is herein incorporated by reference for all purposes.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived PL promoter and N-gene ribosome binding site (Shimatake et al., *Nature* (1981) 292: 128). The particular promoter system is not critical to the invention, any available promoter that functions in prokaryotes can be used.

For expression of soluble, active therapeutic proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*. Promoters are known for other bacterial species, e.g. *Pseudomonas*. See, e.g., U.S. Patent Application Publication No. US 2005/0186666, published Aug. 25, 2005, which is herein incorporated by reference for all purposes.

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

Either constitutive or regulated promoters can be used in the present invention. Regulated promoters can be advantageous because the host cells can be grown to high densities before expression of the fusion proteins is induced. High level expression of heterologous proteins slows cell growth in some situations and may not be desired in all situations, see below. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT Patent Application Publ. No. WO98/20111.

Another inducible promoter is the cspA promoter, which is highly induced at low temperatures in *E. coli*. See, e.g., Sorensen and Mortensen, *Microbial Cell Factories*, 4: 1 (2005) and Mujacic et al. *Gene* 238:325-3332 (1999).

A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. NO. WO098/20111.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra. An auxotrophic expression system is known for *Pseudomonas* species. See, e.g., U.S. Patent Application Publication No. US 2005/0186666, published Aug. 25, 2005, which is herein incorporated by reference for all purposes.

Construction of suitable vectors containing one or more of the above listed components employs standard ligation techniques as described in the references cited above. Isolated plasmids or DNA fragments are cleaved, tailored, and religated in the form desired to generate the plasmids required. To confirm correct sequences in plasmids constructed, the plasmids can be analyzed by standard techniques such as by restriction endonuclease digestion, and/or sequence analysis according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and *Current Protocols in Molecular Biology*, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors.

The methods for introducing the expression vectors into a chosen microorganism that has an oxidizing environment are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The soluble, active therapeutic proteins can be expressed intracellularly, or can be secreted from the cell. Intracellular expression often results in surprisingly high yields. Expression of heterologous proteins, e.g., soluble, active therapeutic proteins, in microorganisms that have an oxidizing intracellular environment can also result is increased expression and activity of heterologous proteins that are directed to the periplasmic space or that are secreted. If necessary, the amount of soluble, active protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the polypeptides are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670). In another embodiment, the soluble, active eukaryotic glycosyltransferase proteins are fused to a subsequence of protein A or bovine serum albumin (BSA), for example, to facilitate purification, secretion, or stability. Computer programs are widely available that allow those of skill to identify amino acid sequences that result in protein secretion or direction to the periplasmic space. See, e.g., Zhang and Hensel, *Protein Science*, 13:2819-2824 (2004); and Bendtsen et al., *J. Mole. Biol.* 340:783-795 (2004).

The soluble, active therapeutic proteins of the invention can also be further linked to other bacterial proteins. This approach often results in high yields, because normal prokaryotic control sequences direct transcription and translation. In *E. coli*, lacZ fusions are often used to express heterologous proteins. Other examples are discussed below. Suitable vectors are readily available, such as the pUR, pEX, and pMR100 series (see, e.g., Sambrook et al., supra.). For certain applications, it may be desirable to cleave the non-glycosyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one recombinant protein may be expressed in a single host cell by placing multiple transcriptional cassettes in a single expression vector, or by utilizing different selectable markers for each of the expression vectors which are employed in the cloning strategy. For example, multiple glycosyltransferases can be expressed in a single cell, e.g., glycosyltransferases that direct N-linked glycosylation or glycosyltransferases that direct O-linked glycosylation.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

After synthesis in a bacterial cell, therapeutic proteins as described herein can be glycosylated in vitro by the soluble, active eukaryotic glycosyltransferase polypeptides described in Provisional U.S. Patent Application No. 60/732,409, filed Oct. 31, 2005 and International Application No. PCT/US06/11065, filed Mar. 24, 2006. Other post-translational modifications of the soluble therapeutic proteins can also be performed, e.g., phosphorylation, or acetylation.

VI. Purification of Soluble, Active Therapeutic Proteins

The soluble, active therapeutic proteins of the present invention are preferably expressed as intracellular proteins. For example, a crude cellular extract containing the expressed intracellular, active therapeutic protein can used in the methods of the present invention.

Alternatively, soluble, active therapeutic protein can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology* Vol. 182: *Guide to Protein Purification*., Academic Press, Inc. N.Y. (1990)). Substantially pure compositions of at least about 70, 75, 80, 85, 90% homogeneity are preferred, and 92, 95, 98 to 99% or more homogeneity are most preferred. The purified proteins may also be used, e.g., as immunogens for antibody production.

To facilitate purification and expression and refolding of the soluble, active therapeutic proteins of the invention, the nucleic acids that encode the proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad CA) vectors pcDNA3.1/Myc-His and pcDNA3.1/V5-His are suitable for expression in mammalian cells). Additional expression vectors suitable for attaching a tag to the therapeutic proteins of the invention, and corresponding detection systems are known to those of skill in the art, and several are commercially available (e.g., FLAG" (Kodak, Rochester NY). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J.K. Setlow, Ed., Plenum Press, NY; commercially available from Qiagen (Santa Clarita, CA)). Other purification or epitope tags include, e.g., AU1, AU5, DDDDK (EC5) (SEQ ID NO:23), E tag, E2 tag, Glu-Glu, a 6 residue peptide, EYMPME (SEQ ID NO:24), derived from the Polyoma middle T protein, HA, HSV, IRS, KT3, S tage, S1 tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

Purification tags also include maltose binding domains and starch binding domains. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, *E. coli* thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Starch binding domains, such as a maltose binding domain from *E. coli* and SBD (starch binding domain) from an amylase of *A. niger*, are described in WO 99/15636, herein incorporated by reference. Affinity purification of a fusion protein comprising a starch binding domain using a betacyclodextrin (BCD)-derivatized resin is described in WO 2005/014779, published Feb. 17, 2005, herein incorporated by reference in its entirety. In some embodiments, a soluble, active therapeutic protein comprises more than one purification or epitope tag.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the catalytic or functional domains of the soluble, active eukaryotic glycosyltransferase polypeptide or therapeutic protein without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

In preferred embodiments, purification of the therapeutic proteins is simplified by expression of the proteins in microorganisms that have oxidizing environments. Because the solubility of the expressed proteins is enhanced, time consuming purification steps, such as solubilization, denaturation, and refolding, can be omitted from a purification protocol. In some embodiments, the bacterially-expressed therapeutic protein exhibits enzymatic or biological activity without in vitro post-translational processing, e.g., glycosylation or phosphorylation.

It must be noted that as used herein and in the appended claims, the singular forms "a", "and", and "the" include plural referents unless the context clearly dictates otherwise. Thus, for example, reference to "a cell" includes a plurality of such cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citations are incorporated herein by reference.

EXAMPLES

Example 1

Expression of Therapeutic Proteins in trxB gor Supp Mutant E. coli

General Procedures

Therapeutic proteins tested were human Fibroblast Growth Factor-20 (FGF-20) (SEQ ID NO:1), Fibroblast Growth Factor-21 (FGF-21) (SEQ ID NO:2), Glucocerebrosidase (SEQ ID NO:3), Neurotrophin-3 (NT-3) alone (SEQ ID NO:4) or a fusion of pro-NT-3 to the maltose binding protein (MBP) tag (SEQ ID NO:5), two mutant forms of growth hormone (GH) (SEQ ID NO:6 and (SEQ ID NO:7), and Granulocyte Colony Stimulating Factor (G-CSF) (SEQ ID NO:8). Examples of, e.g., human FGF-20, human FGF-21, G-CSF, and human growth hormone and other mutants are disclosed in e.g., WO 2004/103275, WO 2005/055946, WO 2005/070138, International application PCT/US05/039226, filed Oct. 31, 2005, and published as WO06/050247; International application PCT/US06/013903, filed Apr. 10, 2006; and US Provisional Application No. 60/832,461, filed Jul. 21, 2006; each of which is herein incorporated by reference for all purposes. Many constructs, including FGF-21, NT-3, and GH constructs, lacked their N-terminal signal sequences, but retained an amino-terminal methionine. Nucleic acids encoding codon-optimized versions of these therapeutic proteins were commercially designed and synthesized, and mutations introduced by PCR. For non-tagged constructs, the synthetic genes were subcloned using flanking 5' NdeI and 3' XhoI or 3' EcoRI sites into up to five different expression vector backbones: Vector1, pCWin2 (see, e.g., WO 2005/067601); Vector2, derived from pCWin2, modified leader sequence, truncated promoter; Vector3, derived from pCWin2, modified leader sequence; Vector4, pET24a; Vector5, derived from pCWin2, alternate leader sequence. For the MBP-pro-NT-3 construct, nucleic acids encoding the MBP tag were subcloned into Vector1 as a NdeI-BamHI fragment from pMAL-c2g. The synthetic codon-optimized NT-3 prodomain was subcloned as a BamHI-BsiWI fragment, and the 5' end of the mature NT-3 open reading frame was modified by PCR to contain a compatible BsiWI site. PCR, cloning, and bacterial transformations were performed using standard techniques (e.g. Current Protocols in Molecular Biology, Ausubel, FM, et al, eds. John Wiley & Sons, Inc. 1998). These constructs were tested in one or more of four different E. coli strains: W3110, BL21 DE3, a trxB gor supp mutant strain, and a DE3 trxB gor supp mutant strain.

For protein expression, an overnight small scale culture was used to inoculate a 50-150 mL culture of prewarmed animal-free LB containing 50 µg/ml kanamycin. The culture was incubated at 37° C. with shaking, and monitored at $OD_{620}$. When the $OD_{620}$ reached 0.4-0.6, the cultures were split and transferred to a 37° C. or 20° C. shaking incubator for 15-20 minutes. IPTG was then added to 0.01-1.0 mM final concentration, and shaking incubation was continued for 1.5 hours up to 16-20 hours. Cells were harvested by centrifugation at 4° C., 7000×g for 15 mins.

For total cell extract analysis of protein expression, cells from an aliquot of the induced cultures were collected by centrifugation and lysed in PBS/0.1% SDS. Samples were resolved by SDS-PAGE, and stained with Coomassie fluorescent orange.

For the analysis of protein solubility, bacterial cells from 50-150 mL of induced cultures were collected by centrifugation and resuspended using 10-50 mL of lysis buffer (eg PBS, 5 mM EDTA), and lysed by mechanical disruption with three passes through a microfluidizer. Small samples were taken and insoluble material was pelleted by centrifugation for 10 minutes at top speed at 4° C. in a microcentrifuge. The supernatant was then separated from the pellet, and both were analyzed by SDS-PAGE and protein staining.

Fibroblast Growth Factor-20

Vectors bearing FGF-20 were transformed into W3110, BL21 DE3, trxB gor supp mutant, and DE3 trxB gor supp mutant E. coli strains. Cultures (50-100 mL), induced at varied temperatures and times, were analyzed for protein expression. As shown in FIG. 1a, expression was observed with Vectors 2-4. Expression was observed as soon as 1.5 hours after induction, and greater levels of expression were at 37° C. than 20° C.

Figure 1B:
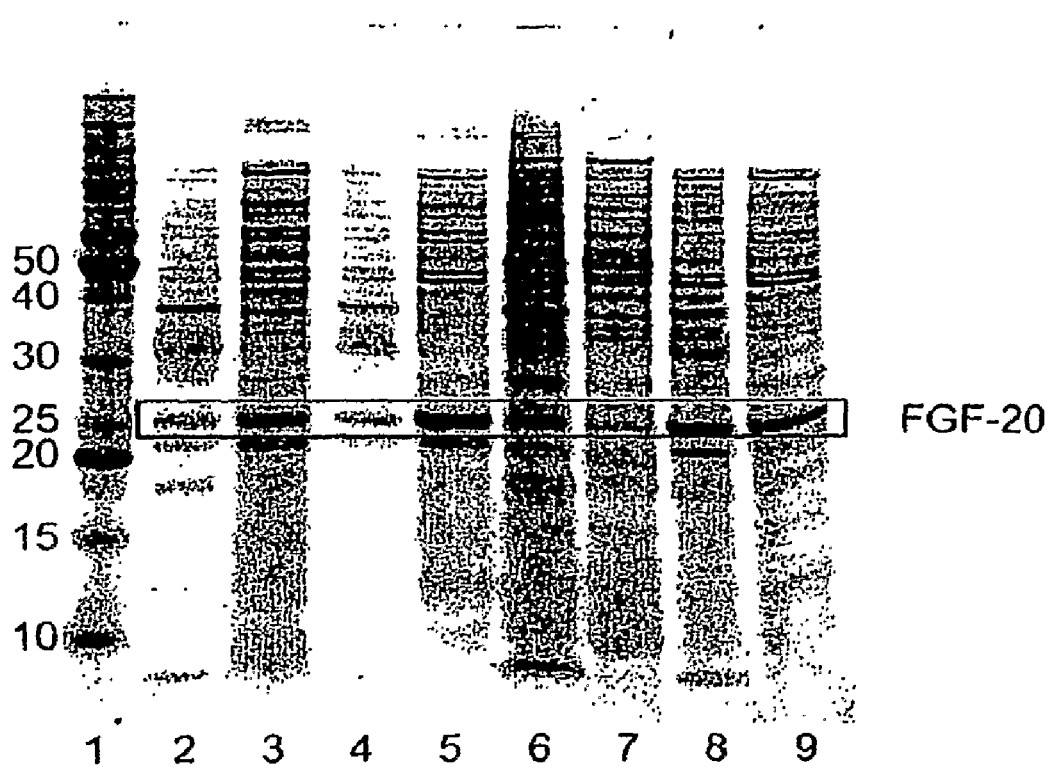
FIG. 1b demonstrates SDS-PAGE analysis of the solubility of human FGF-20 when expressed in different *E. coli* strains. Human FGF-20 was expressed from pET24a vector in the *E. coli* strain BL21 DE3 at 37° C. (lanes 6-7), and in a trxB gor supp mutant DE3 *E. coli* strain at 20° C. (lanes 2-3), 30° C. (lanes 4-5), and 37° C. (lanes 8-9). Following lysis, cellular protein was fractionated by centrifugation into insoluble fractions (lanes 2, 4, 6, 8) or soluble fractions (lanes 3, 5, 7, 9). A box indicates the position of human FGF-20 in the gel. The first lane is molecular weight markers.

Cells from induced BL21 DE3 and trxB gor supp mutant DE3 cultures bearing Vector4 FGF-20 were lysed and analyzed for protein solubility. As shown in FIG. 1b, the majority of FGF-20 was expressed as a soluble protein in the trxB gor supp mutant DE3 cells when grown at 20° C. and at 30° C.

Fibroblast Growth Factor-21

Figure 2A:
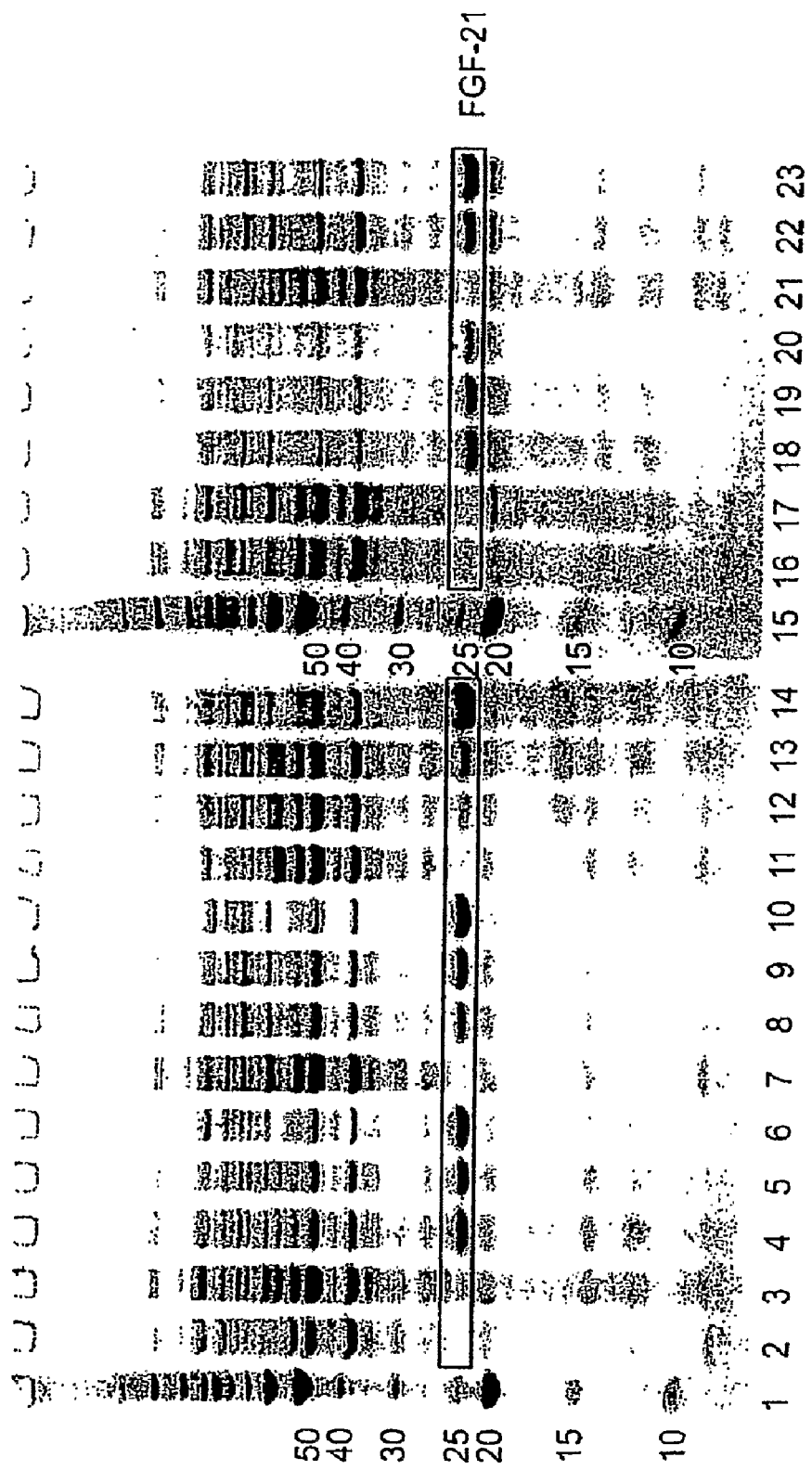
FIG. 2a demonstrates expression of human fibroblast growth factor 21 (FGF-21) in different *E. coli* strains. Nucleic acids encoding mature human FGF-21 were cloned into Vector1 (lanes 3, 7, 11, 17, 21), Vector2 (lanes 4, 8, 12, 18, 22), Vector3 (lanes 5, 9, 13, 19, 23), and Vector4 (lanes 6, 10, 14, 20). These constructs were tested for expression in *E. coli* strain W3110 (lanes 2-5, 7-9, 11-13, 16), BL21 DE3 (lanes 6, 10, 14), trxB gor supp mutant (lanes 17-19, 21-23) and trxB gor supp mutant DE3 (lane 20). For comparison, W3110 bearing Vector1 without an insert was included in lanes 2 and 16. Cells were harvested after 1.5 hours (lanes 2-6, 16) or overnight (lanes 7-14, 17-23) induction at 37° C. (lanes 2-10, 16-20) or 20° C. (lanes 11-14, 21-23). Total cell extracts were analyzed by SDS-PAGE. A box indicates the position of human FGF-21 in the gel. Molecular weight markers were run in lanes 1 and 15.

Vectors bearing FGF-21 were transformed into W3110, BL21 DE3, trxB gor supp mutant, and DE3 trxB gor supp mutant E. coli strains. Cultures (100 mL), varied by induction temperature and time, were analyzed for protein expression. As shown in FIG. 2a, expression was observed in strains with FGF-21 in Vectors2-4. Expression was observed as soon as 1.5 hours after induction.

Figure 2B:
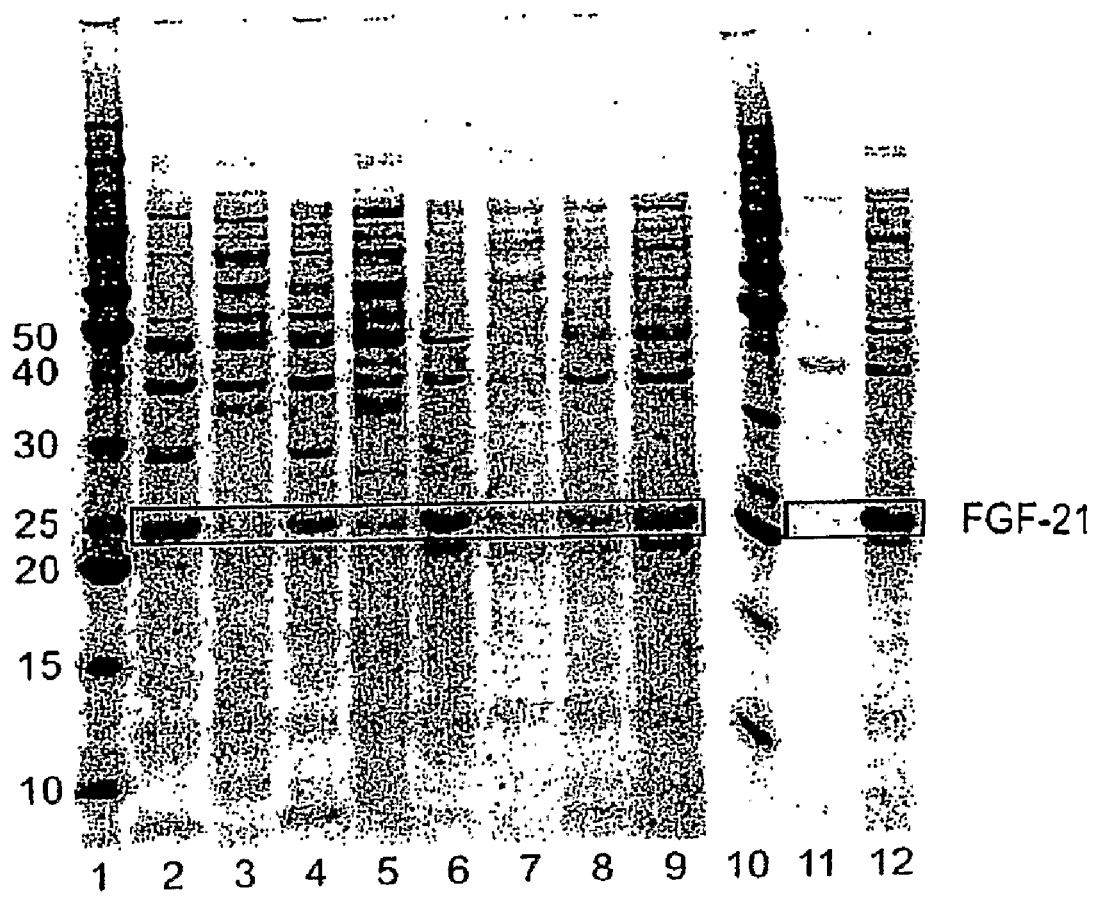
FIG. 2b demonstrates the SDS-PAGE analysis of solubility of human FGF-21 when expressed in different E. coli strains. Human FGF-21 was expressed from Vector3 in E. coli strain W3110 at 37° C. (lanes 2-3) and 20° C. (lanes 4-5), and in a trxB gor supp mutant E. coli strain at 37° C. (lanes 6-7), 20° C. (lanes 8-9), and 18° C. (lanes 11-12). Following lysis, cellular protein was fractionated by centrifugation into insoluble fractions (lanes 2, 4, 6, 8, 11) or soluble fractions (lanes 3, 5, 7, 9, 12). A box indicates the position of human FGF-21 in the gel. Lanes 1 and 10 are molecular weight markers.
Figure 2C:
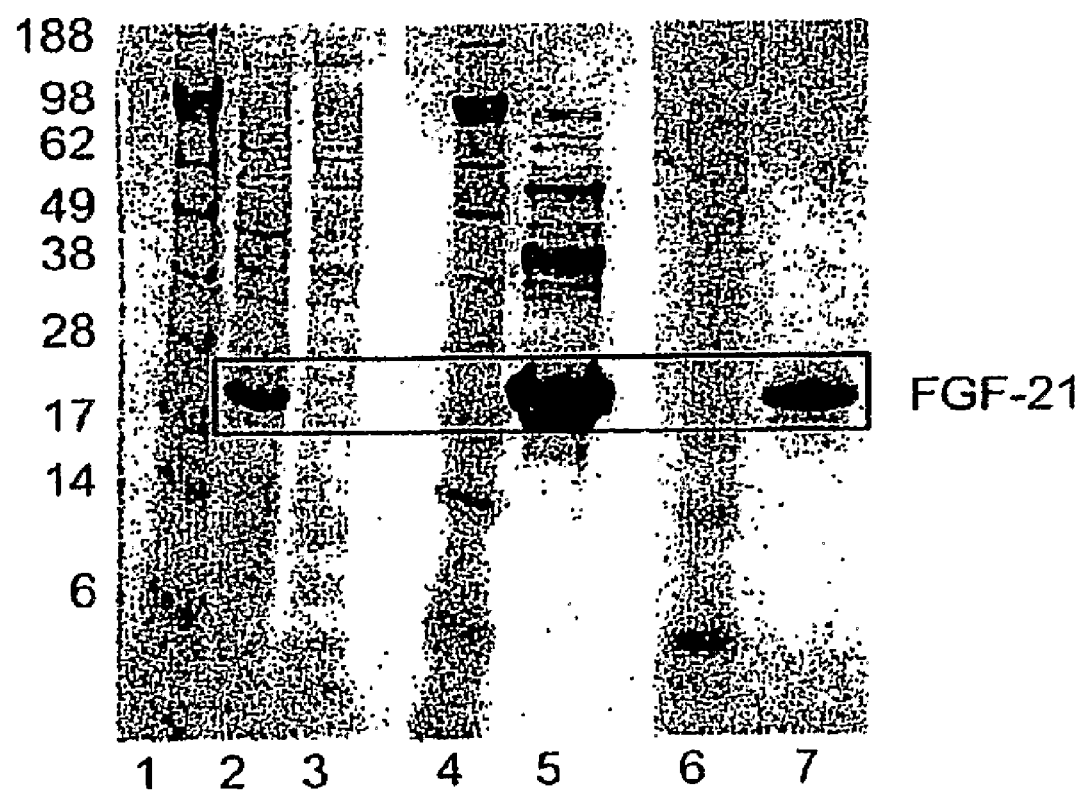
FIG. 2c provides the purification of human FGF-21 produced in trxB gor supp mutant E. coli. Nucleic acids encoding a mature form of human FGF-21 were cloned into Vector3. Cells bearing the human FGF-21 expression construct were induced overnight with 0.1 mM IPTG at 20° C. Induced cells were collected by centrifugation, lysed, and the cell lysate was clarified by centrifugation (lane 2). Human FGF-21 was captured from the supernatant by passage over a HiTrap Q fast flow column, washed, and eluted with a NaCl gradient (flow thru shown in lane 3). Peak human FGF-21 QFF fractions were pooled (lane 5), and further purified by size exclusion chromatography using a Superdex 75 column (lanes 7). Purification step samples were analyzed by SDS-PAGE and Coomassie stained (lanes 1-7). An arrow indicates the position of human FGF21 in the gel. Molecular weight markers were run in lanes 1, 4, and 6.
Figure 2D:
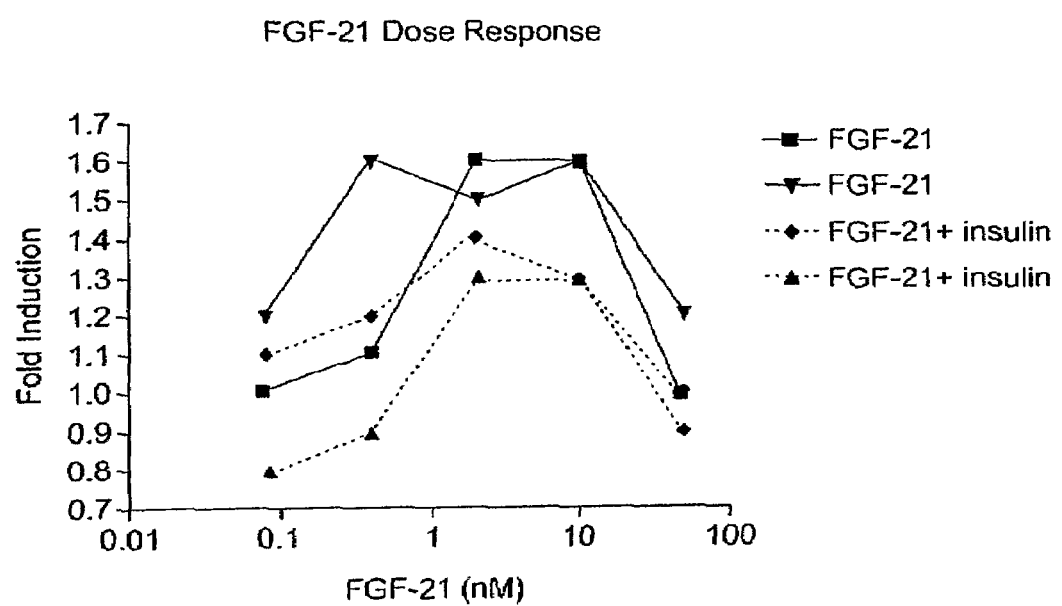
FIG. 2d demonstrates the biological activity of purified human FGF21 on primary human adipocytes. A dilution series of FGF-21 was added to human adipocytes in vitro, either in the presence or absence of insulin, and challenged with radioactively labeled glucose to test uptake. The results were normalized to glucose uptake in the absence of FGF-21.

Cells from induced cultures of W3110 and trxB gor supp mutant strains bearing Vector3 FGF-21 were analyzed for protein solubility. As shown in FIG. 2b, the majority of FGF-21 was soluble in the trxB gor supp mutant cells when grown at 18-20° C. Soluble FGF-21 was further purified by standard chromatographic techniques (FIG. 2c), and demonstrated to be active in a primary adipocyte glucose uptake assay (FIG. 2d). See, e.g., Kharitonenkov, A. et al., *J. Clin. Invest.*, 115: 1627-1635 (2005).

Glucocerebrosidase

Figure 3:
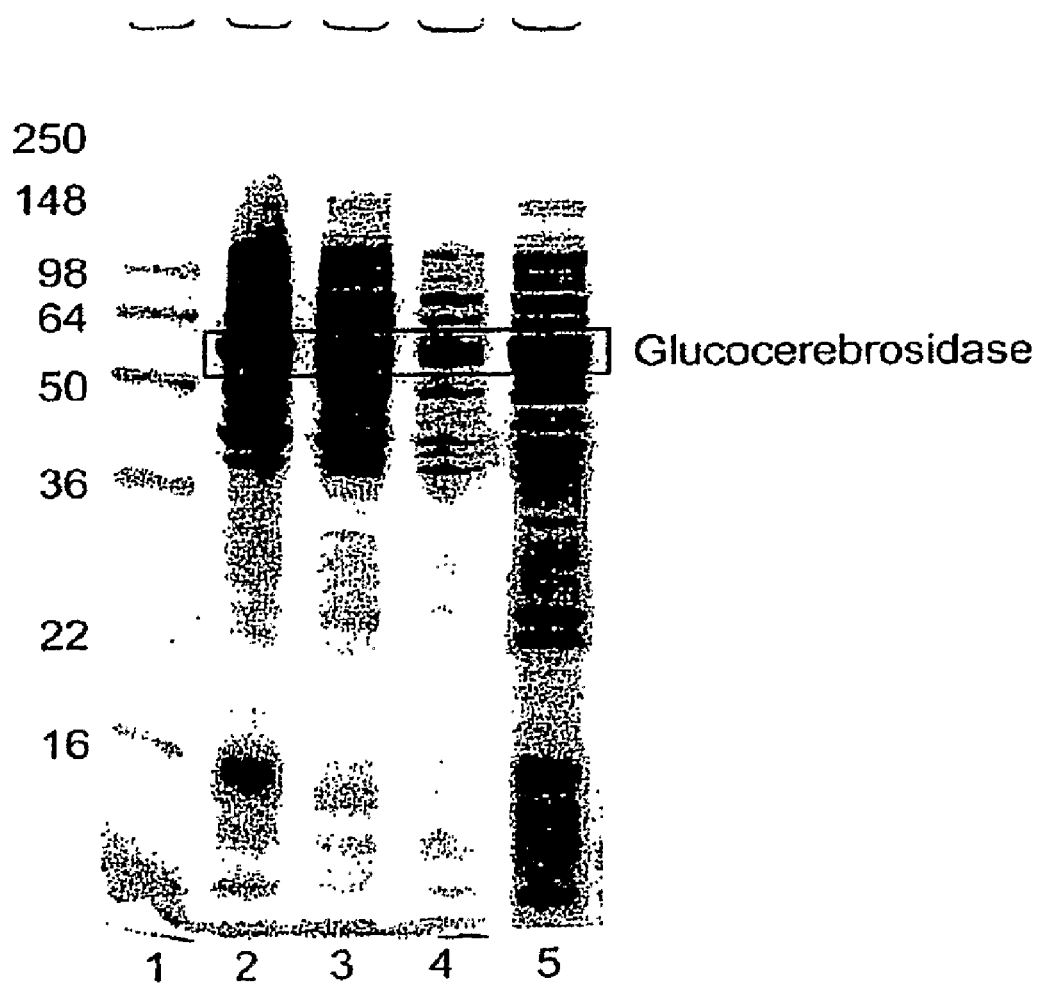
FIG. 3 demonstrates the expression and solubility of human glucocerebrosidase when expressed in different E. coli strains. Nucleic acids encoding truncated glucocerebrosidase were cloned into Vector1, and tested for expression and solubility in E. coli strain W3110 at 37° C. (lanes 2-3), and in a trxB gor supp mutant E. coli strain at 20° C. (lanes 4-5). Cells were harvested after overnight incubation in induction medium with IPTG. Following lysis, cellular protein was fractionated by centrifugation into insoluble fractions (lanes 2 and 4) or soluble fractions (lanes 3 and 5). Protein fractions were analyzed by SDS-PAGE. A box indicates the position of human glucocerebrosidase in the gel. The first lane is molecular weight markers.

Vector1 bearing a truncated version of human glucocerebrosidase was transformed into W3110 and trxB gor supp mutant strains. Cells from cultures (150 mL) of W3110 induced at 37° C. and trxB gor supp mutant cells induced at 20° C. were analyzed for protein solubility. As shown in FIG. 3, glucocerebrosidase was insoluble when expressed in W3110 cells. By contrast, the glucocerebrosidase was soluble when expressed in trxB gor supp mutant strain. When assayed for glucocerebrosidase activity by literature methods, the trxB gor supp mutant lysate was found to be enzymatically active. Glucocerebrosidase assays are known to those of skill and are disclosed, e.g., at Choy and Davidson, *Pediat. Res.*, 14:54-59(1980); and Choy, *Hum. Genet.*, 67:432-436 (1984).

Neurotrophin-3

Figure 4:
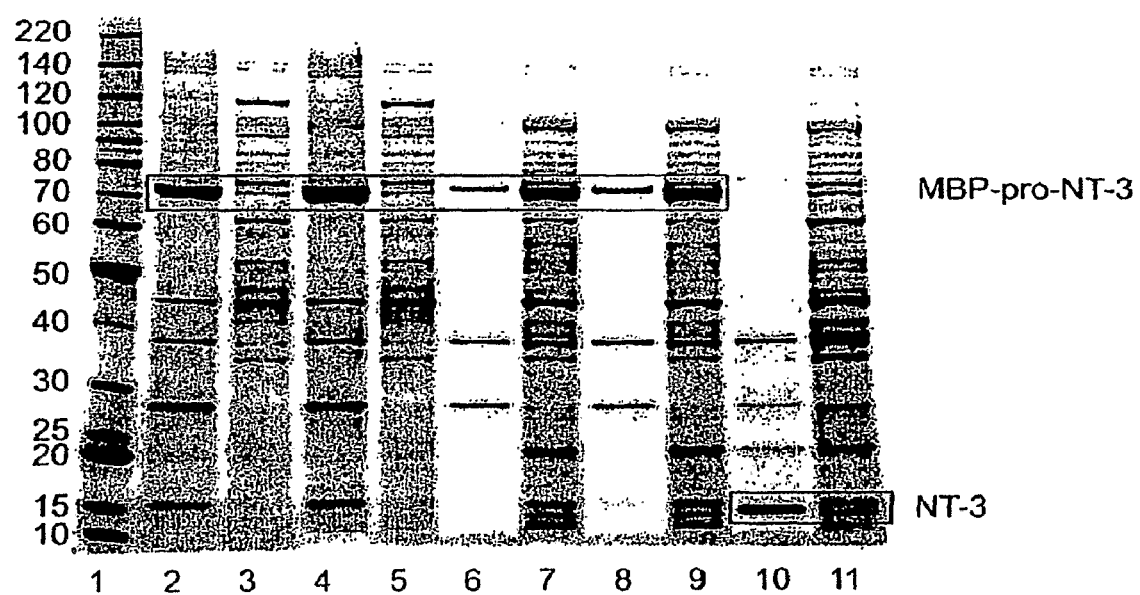
FIG. 4 demonstrates the solubility of human Neurotrophin-3 (NT-3) and MBP-tagged pro-NT-3 when expressed in different E. coli strains. Nucleic acids encoding mature human NT-3 cloned into Vector3 (lanes 10-11), and two forms of MBP-tagged pro-NT-3 cloned into Vector1 (lanes 2-9) were tested for expression and solubility in E. coli strain W3110 at 37° C. (lanes 2-5), and in a trxB gor supp mutant E. coli at 20° C. (lanes 6-11). Cells were harvested after overnight incubation in induction medium with IPTG. Following lysis, cellular protein was fractionated by centrifugation into insoluble fractions (lanes 2, 4, 6, 8, 10) or soluble fractions (lanes 3, 5, 7, 9, 11). Protein fractions were analyzed by SDS-PAGE. boxes indicate the positions of mature NT-3 and MBP-tagged pro-NT-3 in the gel. The first lane is molecular weight markers.

Vectors bearing human Neurotrophin-3 (NT-3) or MBP-tagged pro-NT-3 were transformed into W3110 and trxB gor supp mutant strains. Cells from cultures (100 mL) of the W3110 strain induced at 37° C. and the trxB gor supp mutant strain induced at 20° C. were analyzed for protein solubility. As shown in FIG. 4, NT-3 was insoluble when expressed in trxB gor supp mutant cells. Similarly, MBP-pro-NT-3 was insoluble when expressed in W3110 cells. By contrast, a substantial fraction of total MBP-pro-NT-3 was soluble when expressed in trxB gor supp mutant cells.

Growth Hormone

Vector4 bearing mutant forms of human GH was transformed into DE3 trxB gor supp mutant E. coli. Cells from cultures induced at 20° C. with either 10 or 100 µM IPTG were analyzed for protein induction and solubility. As shown in FIG. 5A, expression mutant human GH was strongly induced with both concentrations of IPTG, and GH was soluble in extracts from both cultures.

Figure 6A:
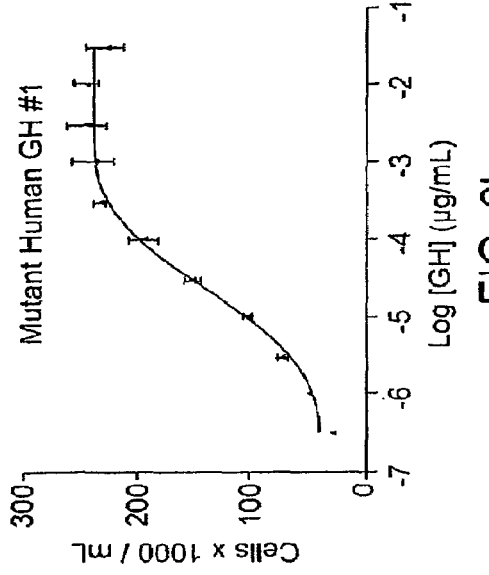
FIG. 6 demonstrates the biological activity of native and mutant forms of human growth hormone (GH). Commercially available native human GH (panel A) and purified mutant forms of GH expressed in trxB gor supp mutant E. coli (panel B, mutant GH #1, seq. ID #7; panel C, mutant GH #2, seq. ID #8) were assayed for GH-dependent growth of NB211 cells. See, e.g., Patra, et al., Protein Expr. Purif. 18: 182-192 (2000).
Figure 6B:
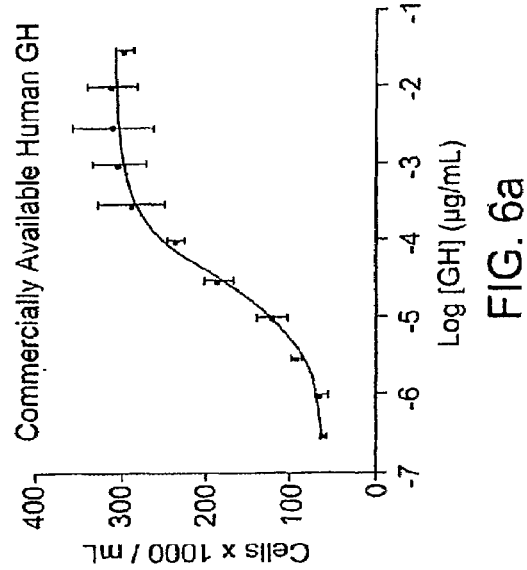
Figure 6C:
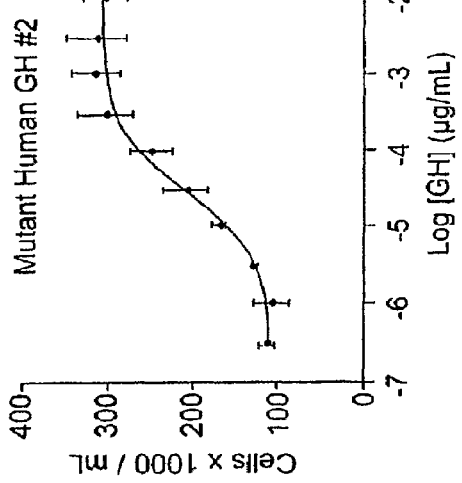

Mutant human GH solubly expressed in DE3 trxB gor supp mutant E. coli was further purified (FIG. 5B) and analyzed for biological activity (FIG. 6). Larger induction cultures (1 L) prepared as described above were resuspended at 4 g wet cell pellet per 100 ml lysis buffer (20 mM Tris pH 8.5, 5 mM EDTA) and lysed by two passes through a microfluidizer. The lysate was partially clarified by centrifugation at 7,000×g, 4° C. for 20 minutes. Polyethylene imine (PEI) was added to a final concentration of 0.1%, and the supernatant was stirred at 4° C. for one hour. The lysate was then further clarified by centrifugation at 20,000×g, 4° C. for 20 minutes. Following 0.45 µm filtration, human GH in the supernatant was captured on a HiTrap DEAE fast flow column. The column was washed with excess lysis buffer, and the GH eluted with a 0-200 mM NaCl gradient. Peak human GH fractions were pooled, concentrated, and desalted into 10 mM sodium phosphate, pH 7.2. The desalted human GH was then passed through a ceramic hydroxyapatite column, concentrated, and polished by size exclusion chromatography on a Superdex 75 column. Growth-inducing activities of purified mutant forms of GH as compared to commercially available native GH were assayed on Nb2-11 cells using standard techniques (FIG. 6). Nb2-11 cell proliferation assays were used to determine the in vitro activity of the control hGH proteins and bacterially-expressed hGH mutant proteins. The assay was based that described in Patra, et al., *Protein Expr. Purif.* 18:182-192 (2000). No or very slight differences in activity levels were seen when the bacterially expressed human GH proteins were compared to the control commercially available native GH.

Granulocyte Colony Stimulating Factor

Figure 7:
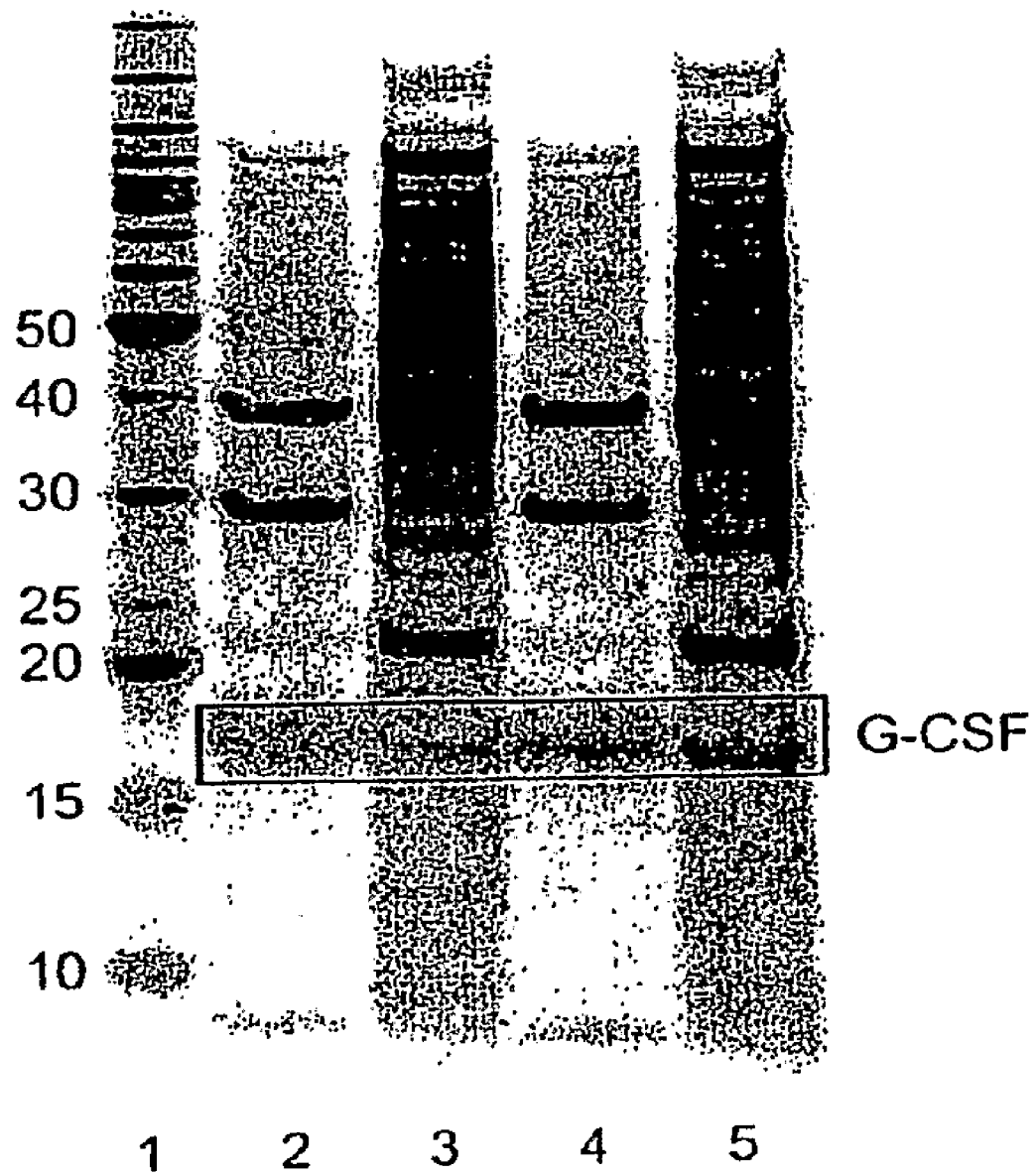
FIG. 7 demonstrates the expression and solubility of human granulocyte-colony stimulating factor (G-CSF) when expressed in trxB gor supp mutant E. coli. Two nucleic acids encoding truncated G-CSF were cloned into Vector5, and tested for expression and solubility in trxB gor supp mutant E. coli at 20° C. Cells were harvested after overnight incubation in induction medium with IPTG. Following lysis, cellular protein was fractionated by centrifugation into insoluble fractions (lanes 2 and 4) or soluble fractions (lanes 3 and 5). Protein fractions were analyzed by SDS-PAGE. A box indicates the position of human G-CSF in the gel. The first lane is molecular weight markers.

Two different synthetic DNA sequences encoding the same G-CSF amino acid sequence (SEQ ID NO:8) carried on Vector5 were transformed into trxB gor supp mutant E. coli. Protein expression was induced at 20° C. for approximately 16 hours with 0.5 mM IPTG, and cell lysates analyzed for G-CSF expression and solubility. As shown in FIG. 7, G-CSF was expressed in both cultures with approximately 40% in the soluble fraction.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of producing soluble fibroblast growth factor 21 (FGF-21) in a microorganism, wherein the microorganism has an oxidizing intracellular environment, which method comprises the steps of
   a) expressing in the microorganism a nucleic acid that encodes FGF-21 and
   b) growing the microorganism at a temperature of 15-20° C. under conditions that allow production of soluble FGF-21.

2. The method of claim 1, wherein the microorganism is an E. coli.

3. The method of claim 2, wherein the E. coli has a mutation in the txrB gene and a gor gene.

4. The method of claim 2, wherein the nucleic acid is expressed under the control of an inducible promoter.

5. The method of claim 1, wherein the microorganism has a mutation in an endogeneous reductase nucleic acid.

6. The method of claim 1, further comprising the step of isolating the soluble FGF-21.

7. The method of claim 1, wherein the soluble FGF-21 is produced on a commercial scale.

8. The method of claim 1, wherein the FGF-21 comprises a purification tag.

9. The method of claim 1, wherein the microorganism comprises a heterologous protein disulfide isomerase (PDI).

10. The method of claim 1, wherein the microorganism comprises a heterologous chaperone protein.

11. The method of claim 1, wherein the FGF-21 exhibits enzymatic or biological activity.

12. The method of claim 1, wherein the oxidizing intracellular environment has a ratio of reduced glutathione (GSH) to oxidized glutathione (GSSG) that is less than 40.

* * * * *

SEQUENCE LISTING

<160> NUMBER OF SEQ ID NOS: 24

<210> SEQ ID NO 1
<211> LENGTH: 211
<212> TYPE: PRT
<213> ORGANISM: Homo sapiens
<220> FEATURE:
<223> OTHER INFORMATION: fibroblast growth factor 20 (FGF-20)

<400> SEQUENCE: 1

Met Ala Pro Leu Ala Glu Val Gly Gly Phe Leu Gly Gly Leu Glu Gly
1               5                   10                  15

Leu Gly Gln Gln Val Gly Ser His Phe Leu Pro Pro Ala Gly Glu
            20                  25                  30

Arg Pro Pro Leu Gly Glu Arg Ser Ala Ala Glu Arg Ser Ala
            35                  40                  45

Arg Gly Gly Pro Gly Ala Ala Gln Leu Ala His Leu His Gly Ile Leu
    50                  55                  60

Arg Arg Arg Gln Leu Tyr Cys Arg Thr Gly Phe His Leu Gln Ile Leu
65                  70                  75                  80

Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
                100                 105                 110

Val Asp Ser Gly Leu Tyr Leu Gly Met Asn Asp Lys Gly Glu Leu Tyr
            115                 120                 125

Gly Ser Glu Lys Leu Thr Ser Glu Cys Ile Phe Arg Glu Gln Phe Glu
130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
            180                 185                 190

Arg Pro Val Asp Pro Glu Arg Val Pro Glu Leu Tyr Lys Asp Leu Leu
        195                 200                 205

Met Tyr Thr
    210

<210> SEQ ID NO 2
<211> LENGTH: 209
<212> TYPE: PRT
<213> ORGANISM: Homo sapiens
<220> FEATURE:
<223> OTHER INFORMATION: mature fibroblast growth factor 21 (FGF-21)

<400> SEQUENCE: 2

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
130                 135                 140

```
His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
            165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser

<210> SEQ ID NO 3
<211> LENGTH: 499
<212> TYPE: PRT
<213> ORGANISM: Homo sapiens
<220> FEATURE:
<223> OTHER INFORMATION: glucocerebrosidase

<400> SEQUENCE: 3

Met Gly Ala Arg Pro Cys Ile Pro Lys Ser Phe Gly Tyr Ser Ser Val
1               5                   10                  15

Val Cys Val Cys Asn Ala Thr Tyr Cys Asp Ser Phe Asp Pro Pro Thr
            20                  25                  30

Phe Pro Ala Leu Gly Thr Phe Ser Arg Tyr Glu Ser Thr Arg Ser Gly
        35                  40                  45

Arg Arg Met Glu Leu Ser Met Gly Pro Ile Gln Ala Asn His Thr Gly
50                  55                  60

Thr Gly Leu Leu Leu Thr Leu Gln Pro Glu Gln Lys Phe Gln Lys Val
65                  70                  75                  80

Lys Gly Phe Gly Gly Ala Met Thr Asp Ala Ala Ala Leu Asn Ile Leu
            85                  90                  95

Ala Leu Ser Pro Pro Ala Gln Asn Leu Leu Leu Lys Ser Tyr Phe Ser
            100                 105                 110

Glu Glu Gly Ile Gly Tyr Asn Ile Ile Arg Val Pro Met Ala Ser Cys
            115                 120                 125

Asp Phe Ser Ile Arg Thr Tyr Thr Tyr Ala Asp Thr Pro Asp Asp Phe
    130                 135                 140

Gln Leu His Asn Phe Ser Leu Pro Glu Glu Asp Thr Lys Leu Lys Ile
145                 150                 155                 160

Pro Leu Ile His Arg Ala Leu Gln Leu Ala Gln Arg Pro Val Ser Leu
                165                 170                 175

Leu Ala Ser Pro Trp Thr Ser Pro Thr Trp Leu Lys Thr Asn Gly Ala
            180                 185                 190

Val Asn Gly Lys Gly Ser Leu Lys Gly Gln Pro Gly Asp Ile Tyr His
            195                 200                 205

Gln Thr Trp Ala Arg Tyr Phe Val Lys Phe Leu Asp Ala Tyr Ala Glu
    210                 215                 220

His Lys Leu Gln Phe Trp Ala Val Thr Ala Glu Asn Glu Pro Ser Ala
225                 230                 235                 240

Gly Leu Leu Ser Gly Tyr Pro Phe Gln Cys Leu Gly Phe Thr Pro Glu
                245                 250                 255

His Gln Arg Asp Phe Ile Ala Arg Asp Leu Gly Pro Thr Leu Ala Asn
            260                 265                 270

Ser Thr His His Asn Val Arg Leu Leu Met Leu Asp Asp Gln Arg Leu
            275                 280                 285

Leu Leu Pro His Trp Ala Lys Val Val Leu Thr Asp Pro Glu Ala Ala
    290                 295                 300
```

```
Lys Tyr Val His Gly Ile Ala Val His Trp Tyr Leu Asp Phe Leu Ala
305                 310                 315                 320

Pro Ala Lys Ala Thr Leu Gly Glu Thr His Arg Leu Phe Pro Asn Thr
            325                 330                 335

Met Leu Phe Ala Ser Glu Ala Cys Val Gly Ser Lys Phe Trp Glu Gln
        340                 345                 350

Ser Val Arg Leu Gly Ser Trp Asp Arg Gly Met Gln Tyr Ser His Ser
    355                 360                 365

Ile Ile Thr Asn Leu Leu Tyr His Val Val Gly Trp Thr Asp Trp Asn
370                 375                 380

Leu Ala Leu Asn Pro Glu Gly Gly Pro Asn Trp Val Arg Asn Phe Val
385                 390                 395                 400

Asp Ser Pro Ile Ile Val Asp Ile Thr Lys Asp Thr Phe Tyr Lys Gln
            405                 410                 415

Pro Met Phe Tyr His Leu Gly His Phe Ser Lys Phe Ile Pro Glu Gly
        420                 425                 430

Ser Gln Arg Val Gly Leu Val Ala Ser Gln Lys Asn Asp Leu Asp Ala
    435                 440                 445

Val Ala Leu Met His Pro Asp Gly Ser Ala Val Val Val Val Leu Asn
450                 455                 460

Arg Ser Ser Lys Asp Val Pro Leu Thr Ile Lys Asp Pro Ala Val Gly
465                 470                 475                 480

Phe Leu Glu Thr Ile Ser Pro Gly Tyr Ser Ile His Thr Tyr Leu Trp
            485                 490                 495

Arg Arg Gln

<210> SEQ ID NO 4
<211> LENGTH: 120
<212> TYPE: PRT
<213> ORGANISM: Homo sapiens
<220> FEATURE:
<223> OTHER INFORMATION: Neurotrophin 3 (NT-3)

<400> SEQUENCE: 4

Met Tyr Ala Glu His Lys Ser His Arg Gly Glu Tyr Ser Val Cys Asp
1               5                   10                  15

Ser Glu Ser Leu Trp Val Thr Asp Lys Ser Ser Ala Ile Asp Ile Arg
            20                  25                  30

Gly His Gln Val Thr Val Leu Gly Glu Ile Lys Thr Gly Asn Ser Pro
        35                  40                  45

Val Lys Gln Tyr Phe Tyr Glu Thr Arg Cys Lys Glu Ala Arg Pro Val
    50                  55                  60

Lys Asn Gly Cys Arg Gly Ile Asp Asp Lys His Trp Asn Ser Gln Cys
65                  70                  75                  80

Lys Thr Ser Gln Thr Tyr Val Arg Ala Leu Thr Ser Glu Asn Asn Lys
                85                  90                  95

Leu Val Gly Trp Arg Trp Ile Arg Ile Asp Thr Ser Cys Val Cys Ala
            100                 105                 110

Leu Ser Arg Lys Ile Gly Arg Thr
        115                 120

<210> SEQ ID NO 5
<211> LENGTH: 637
<212> TYPE: PRT
<213> ORGANISM: Artificial Sequence
<220> FEATURE:
<223> OTHER INFORMATION: synthetic MBP-tagged pro-NT-3
```

<400> SEQUENCE: 5

```
Met Lys Thr Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
 50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Pro
    370                 375                 380

Gly Ala Ala His Tyr Val Glu Phe Gly Ser His Met Gln Gly Asn Asn
385                 390                 395                 400

Met Asp Gln Arg Ser Leu Pro Glu Asp Ser Leu Asn Ser Leu Ile Ile
                405                 410                 415
```

```
Lys Leu Ile Gln Ala Asp Ile Leu Lys Asn Lys Leu Ser Lys Gln Met
            420                 425                 430

Val Asp Val Lys Glu Asn Tyr Gln Ser Thr Leu Pro Lys Ala Glu Ala
            435                 440                 445

Pro Arg Glu Pro Glu Arg Gly Gly Pro Ala Lys Ser Ala Phe Gln Pro
        450                 455                 460

Val Ile Ala Met Asp Thr Glu Leu Leu Arg Gln Gln Arg Arg Tyr Asn
465                 470                 475                 480

Ser Pro Arg Val Leu Leu Ser Asp Ser Thr Pro Leu Glu Pro Pro Pro
                485                 490                 495

Leu Tyr Leu Met Glu Asp Tyr Val Gly Ser Pro Val Val Ala Asn Arg
            500                 505                 510

Thr Ser Arg Arg Lys Arg Tyr Ala Glu His Lys Ser His Arg Gly Glu
            515                 520                 525

Tyr Ser Val Cys Asp Ser Glu Ser Leu Trp Val Thr Asp Lys Ser Ser
            530                 535                 540

Ala Ile Asp Ile Arg Gly His Gln Val Thr Val Leu Gly Glu Ile Lys
545                 550                 555                 560

Thr Gly Asn Ser Pro Val Lys Gln Tyr Phe Tyr Glu Thr Arg Cys Lys
                565                 570                 575

Glu Ala Arg Pro Val Lys Asn Gly Cys Arg Gly Ile Asp Asp Lys His
            580                 585                 590

Trp Asn Ser Gln Cys Lys Thr Ser Gln Thr Tyr Val Arg Ala Leu Thr
                595                 600                 605

Ser Glu Asn Asn Lys Leu Val Gly Trp Arg Trp Ile Arg Ile Asp Thr
            610                 615                 620

Ser Cys Val Cys Ala Leu Ser Arg Lys Ile Gly Arg Thr
625                 630                 635

<210> SEQ ID NO 6
<211> LENGTH: 192
<212> TYPE: PRT
<213> ORGANISM: Homo sapiens
<220> FEATURE:
<223> OTHER INFORMATION: Mutant GH #1

<400> SEQUENCE: 6

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
            115                 120                 125

Leu Glu Asp Gly Ser Pro Thr Ile Asn Thr Ile Phe Lys Gln Thr Tyr
        130                 135                 140
```

-continued

```
Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 7
<211> LENGTH: 192
<212> TYPE: PRT
<213> ORGANISM: Homo sapiens
<220> FEATURE:
<223> OTHER INFORMATION: Mutant GH #2

<400> SEQUENCE: 7

```
Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
                20                  25                  30

Glu Glu Ala Tyr Ile Pro Lys Glu Gln Lys Ala Ser Phe Leu Gln Asn
            35                  40                  45

Pro Gln Thr Ser Leu Cys Phe Ser Glu Ser Ile Pro Thr Pro Ser Asn
50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Ile Asn Thr Ile Ala Asn Gln Thr Ala
130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 8
<211> LENGTH: 175
<212> TYPE: PRT
<213> ORGANISM: Homo sapiens
<220> FEATURE:
<223> OTHER INFORMATION: G-CSF 174 aa form

<400> SEQUENCE: 8

```
Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
50                  55                  60

Cys Pro Ser Gln Ala Leu Gln Leu Ala Gly Cys Leu Ser Gln Leu His
65                  70                  75                  80
```

-continued

```
Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 9
<211> LENGTH: 638
<212> TYPE: PRT
<213> ORGANISM: Escherichia coli
<220> FEATURE:
<223> OTHER INFORMATION: dnaK HSP-70-type molecular chaperone,
      heat-inducible

<400> SEQUENCE: 9

Met Gly Lys Ile Ile Gly Ile Asp Leu Gly Thr Thr Asn Ser Cys Val
1               5                   10                  15

Ala Ile Met Asp Gly Thr Thr Pro Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Phe Lys Ile Ile Ala Ala
                85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Gly Thr Gly Asn Arg Thr Ile Ala Val
            180                 185                 190

Tyr Asp Leu Gly Gly Gly Thr Phe Asp Ile Ser Ile Ile Glu Ile Asp
        195                 200                 205

Glu Val Asp Gly Glu Lys Thr Phe Glu Val Leu Ala Thr Asn Gly Asp
    210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Ile Asp Leu Arg Asn Asp Pro
                245                 250                 255

Leu Ala Met Gln Arg Leu Lys Ala Ala Glu Lys Ala Lys Ile Glu
            260                 265                 270
```

```
Leu Ser Ser Ala Gln Gln Thr Asp Val Asn Leu Pro Tyr Ile Thr Ala
        275                 280                 285

Asp Ala Thr Gly Pro Lys His Met Asn Ile Lys Val Thr Arg Ala Lys
290                 295                 300

Leu Glu Ser Leu Val Glu Asp Leu Val Asn Arg Ser Ile Glu Pro Leu
305                 310                 315                 320

Lys Val Ala Leu Gln Asp Ala Gly Leu Ser Val Ser Asp Ile Asp Asp
                325                 330                 335

Val Ile Leu Val Gly Gly Gln Thr Arg Met Pro Met Val Gln Lys Lys
            340                 345                 350

Val Ala Glu Phe Phe Gly Lys Glu Pro Arg Lys Asp Val Asn Pro Asp
        355                 360                 365

Glu Ala Val Ala Ile Gly Ala Ala Val Gln Gly Gly Val Leu Thr Gly
370                 375                 380

Asp Val Lys Asp Val Leu Leu Leu Asp Val Thr Pro Leu Ser Leu Gly
385                 390                 395                 400

Ile Glu Thr Met Gly Gly Val Met Thr Thr Leu Ile Ala Lys Asn Thr
                405                 410                 415

Thr Ile Pro Thr Lys His Ser Gln Val Phe Ser Thr Ala Glu Asp Asn
            420                 425                 430

Gln Ser Ala Val Thr Ile His Val Leu Gln Gly Glu Arg Lys Arg Ala
        435                 440                 445

Ala Asp Asn Lys Ser Leu Gly Gln Phe Asn Leu Asp Gly Ile Asn Pro
450                 455                 460

Ala Pro Arg Gly Met Pro Gln Ile Glu Val Thr Phe Asp Ile Asp Ala
465                 470                 475                 480

Asp Gly Ile Leu His Val Ser Ala Lys Asp Lys Asn Ser Gly Lys Glu
                485                 490                 495

Gln Lys Ile Thr Ile Lys Ala Ser Ser Gly Leu Asn Glu Asp Glu Ile
            500                 505                 510

Gln Lys Met Val Arg Asp Ala Glu Ala Asn Ala Glu Ala Asp Arg Lys
        515                 520                 525

Phe Glu Glu Leu Val Gln Thr Arg Asn Gln Gly Asp His Leu Leu His
530                 535                 540

Ser Thr Arg Lys Gln Val Glu Glu Ala Gly Asp Lys Leu Pro Ala Asp
545                 550                 555                 560

Asp Lys Thr Ala Ile Glu Ser Ala Leu Thr Ala Leu Glu Thr Ala Leu
                565                 570                 575

Lys Gly Glu Asp Lys Ala Ala Ile Glu Ala Lys Met Gln Glu Leu Ala
            580                 585                 590

Gln Val Ser Gln Lys Leu Met Glu Ile Ala Gln Gln Gln His Ala Gln
        595                 600                 605

Gln Gln Thr Ala Gly Ala Asp Ala Ser Ala Asn Asn Ala Lys Asp Asp
610                 615                 620

Asp Val Val Asp Ala Glu Phe Glu Glu Val Lys Asp Lys Lys
625                 630                 635
```

<210> SEQ ID NO 10
<211> LENGTH: 857
<212> TYPE: PRT
<213> ORGANISM: Escherichia coli
<220> FEATURE:
<223> OTHER INFORMATION: clpB, ClpB protease, ATP dependent

<400> SEQUENCE: 10

Met Arg Leu Asp Arg Leu Thr Asn Lys Phe Gln Leu Ala Leu Ala Asp

-continued

```
1               5               10              15
Ala Gln Ser Leu Ala Leu Gly His Asp Asn Gln Phe Ile Glu Pro Leu
                20              25              30

His Leu Met Ser Ala Leu Leu Asn Gln Glu Gly Gly Ser Val Ser Pro
                35              40              45

Leu Leu Thr Ser Ala Gly Ile Asn Ala Gly Gln Leu Arg Thr Asp Ile
        50              55              60

Asn Gln Ala Leu Asn Arg Leu Pro Gln Val Glu Thr Gly Gly Asp
65              70              75              80

Val Gln Pro Ser Gln Asp Leu Val Arg Val Leu Asn Leu Cys Asp Lys
                85              90              95

Leu Ala Gln Lys Arg Gly Asp Asn Phe Ile Ser Ser Glu Leu Phe Val
                100             105             110

Leu Ala Ala Leu Glu Ser Arg Gly Thr Leu Ala Asp Ile Leu Lys Ala
                115             120             125

Ala Gly Ala Thr Thr Ala Asn Ile Thr Gln Ala Ile Glu Gln Met Arg
        130             135             140

Gly Gly Glu Ser Val Asn Asp Gln Gly Ala Glu Asp Gln Arg Gln Ala
145             150             155             160

Leu Lys Lys Tyr Thr Ile Asp Leu Thr Glu Arg Ala Glu Gln Gly Lys
                165             170             175

Leu Asp Pro Val Ile Gly Arg Asp Glu Glu Ile Arg Arg Thr Ile Gln
                180             185             190

Val Leu Gln Arg Arg Thr Lys Asn Asn Pro Val Leu Ile Gly Glu Pro
        195             200             205

Gly Val Gly Lys Thr Ala Ile Val Glu Gly Leu Ala Gln Arg Ile Ile
        210             215             220

Asn Gly Glu Val Pro Glu Gly Leu Lys Gly Arg Arg Val Leu Ala Leu
225             230             235             240

Asp Met Gly Ala Leu Val Ala Gly Ala Lys Tyr Arg Gly Glu Phe Glu
                245             250             255

Glu Arg Leu Lys Gly Val Leu Asn Asp Leu Ala Lys Gln Glu Gly Asn
                260             265             270

Val Ile Leu Phe Ile Asp Glu Leu His Thr Met Val Gly Ala Gly Lys
        275             280             285

Ala Asp Gly Ala Met Asp Ala Gly Asn Met Leu Lys Pro Ala Leu Ala
        290             295             300

Arg Gly Glu Leu His Cys Val Gly Ala Thr Thr Leu Asp Glu Tyr Arg
305             310             315             320

Gln Tyr Ile Glu Lys Asp Ala Ala Leu Glu Arg Arg Phe Gln Lys Val
                325             330             335

Phe Val Ala Glu Pro Ser Val Glu Asp Thr Ile Ala Ile Leu Arg Gly
                340             345             350

Leu Lys Glu Arg Tyr Glu Leu His His Val Gln Ile Thr Asp Pro
        355             360             365

Ala Ile Val Ala Ala Ala Thr Leu Ser His Arg Tyr Ile Ala Asp Arg
        370             375             380

Gln Leu Pro Asp Lys Ala Ile Asp Leu Ile Asp Glu Ala Ala Ser Ser
385             390             395             400

Ile Arg Met Gln Ile Asp Ser Lys Pro Glu Glu Leu Asp Arg Leu Asp
                405             410             415

Arg Arg Ile Ile Gln Leu Lys Leu Glu Gln Gln Ala Leu Met Lys Glu
                420             425             430
```

```
Ser Asp Glu Ala Ser Lys Lys Arg Leu Asp Met Leu Asn Glu Leu
        435                 440                 445

Ser Asp Lys Glu Arg Gln Tyr Ser Glu Leu Glu Glu Trp Lys Ala
450                 455                 460

Glu Lys Ala Ser Leu Ser Gly Thr Gln Thr Ile Lys Ala Glu Leu Glu
465                 470                 475                 480

Gln Ala Lys Ile Ala Ile Glu Gln Ala Arg Arg Val Gly Asp Leu Ala
                485                 490                 495

Arg Met Ser Glu Leu Gln Tyr Gly Lys Ile Pro Glu Leu Glu Lys Gln
            500                 505                 510

Leu Glu Ala Ala Thr Gln Leu Glu Gly Lys Thr Met Arg Leu Leu Arg
        515                 520                 525

Asn Lys Val Thr Asp Ala Glu Ile Ala Glu Val Leu Ala Arg Trp Thr
530                 535                 540

Gly Ile Pro Val Ser Arg Met Met Glu Ser Glu Arg Glu Lys Leu Leu
545                 550                 555                 560

Arg Met Glu Gln Glu Leu His His Arg Val Ile Gly Gln Asn Glu Ala
                565                 570                 575

Val Asp Ala Val Ser Asn Ala Ile Arg Arg Ser Arg Ala Gly Leu Ala
            580                 585                 590

Asp Pro Asn Arg Pro Ile Gly Ser Phe Leu Phe Leu Gly Pro Thr Gly
        595                 600                 605

Val Gly Lys Thr Glu Leu Cys Lys Ala Leu Ala Asn Phe Met Phe Asp
610                 615                 620

Ser Asp Glu Ala Met Val Arg Ile Asp Met Ser Glu Phe Met Glu Lys
625                 630                 635                 640

His Ser Val Ser Arg Leu Val Gly Ala Pro Pro Gly Tyr Val Gly Tyr
                645                 650                 655

Glu Glu Gly Gly Tyr Leu Thr Glu Ala Val Arg Arg Pro Tyr Ser
            660                 665                 670

Val Ile Leu Leu Asp Glu Val Glu Lys Ala His Pro Asp Val Phe Asn
        675                 680                 685

Ile Leu Leu Gln Val Leu Asp Asp Gly Arg Leu Thr Asp Gly Gln Gly
690                 695                 700

Arg Thr Val Asp Phe Arg Asn Thr Val Val Ile Met Thr Ser Asn Leu
705                 710                 715                 720

Gly Ser Asp Leu Ile Gln Glu Arg Phe Gly Glu Leu Asp Tyr Ala His
                725                 730                 735

Met Lys Glu Leu Val Leu Gly Val Val Ser His Asn Phe Arg Pro Glu
            740                 745                 750

Phe Ile Asn Arg Ile Asp Glu Val Val Val Phe His Pro Leu Gly Glu
        755                 760                 765

Gln His Ile Ala Ser Ile Ala Gln Ile Gln Leu Lys Arg Leu Tyr Lys
770                 775                 780

Arg Leu Glu Glu Arg Gly Tyr Glu Ile His Ile Ser Asp Glu Ala Leu
785                 790                 795                 800

Lys Leu Leu Ser Glu Asn Gly Tyr Asp Pro Val Tyr Gly Ala Arg Pro
                805                 810                 815

Leu Lys Arg Ala Ile Gln Gln Ile Glu Asn Pro Leu Ala Gln Gln
            820                 825                 830

Ile Leu Ser Gly Glu Leu Val Pro Gly Lys Val Ile Arg Leu Glu Val
        835                 840                 845

Asn Glu Asp Arg Ile Val Ala Val Gln
850                 855
```

<210> SEQ ID NO 11
<211> LENGTH: 540
<212> TYPE: PRT
<213> ORGANISM: Escherichia coli
<220> FEATURE:
<223> OTHER INFORMATION: GroEL

<400> SEQUENCE: 11

```
Ala Ala Lys Asp Val Lys Phe Gly Asn Asp Ala Arg Val Lys Met Leu
1               5                   10                  15

Arg Gly Val Asn Val Leu Ala Asp Ala Val Lys Val Thr Leu Gly Pro
            20                  25                  30

Lys Gly Arg Asn Val Val Leu Asp Lys Ser Phe Gly Ala Pro Thr Ile
        35                  40                  45

Thr Lys Asp Gly Val Ser Val Ala Arg Glu Ile Glu Leu Glu Asp Lys
50                  55                  60

Phe Glu Asn Met Gly Ala Gln Met Val Lys Glu Val Ala Ser Lys Ala
65                  70                  75                  80

Asn Asp Ala Ala Gly Asp Gly Thr Thr Thr Ala Thr Val Leu Ala Gln
                85                  90                  95

Ala Ile Ile Thr Glu Gly Leu Lys Ala Val Ala Ala Gly Met Asn Pro
            100                 105                 110

Met Asp Leu Lys Arg Gly Ile Asp Lys Ala Val Thr Ala Ala Val Glu
        115                 120                 125

Glu Leu Lys Ala Leu Ser Val Pro Cys Ser Asp Ser Lys Ala Ile Ala
130                 135                 140

Gln Val Gly Thr Ile Ser Ala Asn Ser Asp Glu Thr Val Gly Lys Leu
145                 150                 155                 160

Ile Ala Glu Ala Met Asp Lys Val Gly Lys Glu Gly Val Ile Thr Val
                165                 170                 175

Glu Asp Gly Thr Gly Leu Gln Asp Glu Leu Asp Val Val Glu Gly Met
            180                 185                 190

Gln Phe Asp Arg Gly Tyr Leu Ser Pro Tyr Phe Ile Asn Lys Pro Glu
        195                 200                 205

Thr Gly Ala Val Glu Leu Glu Ser Pro Phe Ile Leu Leu Ala Asp Lys
210                 215                 220

Lys Ile Ser Asn Ile Arg Glu Met Leu Pro Val Leu Glu Ala Val Ala
225                 230                 235                 240

Lys Ala Gly Lys Pro Leu Leu Ile Ile Ala Glu Asp Val Glu Gly Glu
                245                 250                 255

Ala Leu Ala Thr Leu Val Val Asn Thr Met Arg Gly Ile Val Lys Val
            260                 265                 270

Ala Ala Val Lys Ala Pro Gly Phe Gly Asp Arg Arg Lys Ala Met Leu
        275                 280                 285

Gln Asp Ile Ala Thr Leu Thr Gly Gly Thr Val Ile Ser Glu Glu Ile
290                 295                 300

Gly Met Glu Leu Glu Lys Ala Thr Leu Glu Asp Leu Gly Gln Ala Lys
305                 310                 315                 320

Arg Val Val Ile Asn Lys Asp Thr Thr Thr Ile Ile Asp Gly Val Gly
                325                 330                 335

Glu Glu Ala Ala Ile Gln Gly Arg Val Ala Gln Ile Arg Gln Gln Ile
            340                 345                 350

Glu Glu Ala Thr Ser Asp Tyr Asp Arg Glu Lys Leu Gln Glu Arg Val
        355                 360                 365
```

```
Ala Lys Leu Ala Gly Gly Val Ala Val Ile Lys Val Gly Ala Ala Thr
        370                 375                 380

Glu Val Glu Met Lys Glu Lys Lys Ala Arg Val Glu Asp Ala Leu His
385                 390                 395                 400

Ala Thr Arg Ala Ala Val Glu Glu Gly Val Ala Gly Gly Gly Val
                405                 410                 415

Ala Leu Ile Arg Val Ala Ser Lys Leu Ala Asp Leu Arg Gly Gln Asn
                420                 425                 430

Glu Asp Gln Asn Val Gly Ile Lys Val Ala Leu Arg Ala Met Glu Ala
            435                 440                 445

Pro Leu Arg Gln Ile Val Leu Asn Cys Gly Glu Pro Ser Val Val
        450                 455                 460

Ala Asn Thr Val Lys Gly Gly Asp Gly Asn Tyr Gly Tyr Asn Ala Ala
465                 470                 475                 480

Thr Glu Glu Tyr Gly Asn Met Ile Asp Met Gly Ile Leu Asp Pro Thr
                485                 490                 495

Lys Val Thr Arg Ser Ala Leu Gln Tyr Ala Ala Ser Val Ala Gly Leu
                500                 505                 510

Met Ile Thr Thr Glu Cys Met Val Thr Asp Leu Pro Lys Asn Asp Ala
            515                 520                 525

Ala Asp Leu Gly Ala Ala Gly Gly Met Gly Gly Met
530                 535                 540
```

<210> SEQ ID NO 12
<211> LENGTH: 97
<212> TYPE: PRT
<213> ORGANISM: Oleispira antarctica
<220> FEATURE:
<223> OTHER INFORMATION: Cpn10

<400> SEQUENCE: 12

```
Met Lys Ile Arg Pro Leu His Asp Arg Ile Val Val Arg Arg Lys Glu
1               5                   10                  15

Glu Glu Thr Ala Thr Ala Gly Gly Ile Ile Leu Pro Gly Ala Ala Ala
            20                  25                  30

Glu Lys Pro Asn Gln Gly Val Val Ile Ser Val Gly Thr Gly Arg Ile
        35                  40                  45

Leu Asp Asn Gly Ser Val Gln Ala Leu Ala Val Asn Glu Gly Asp Val
    50                  55                  60

Val Val Phe Gly Lys Tyr Ser Gly Gln Asn Thr Ile Asp Ile Asp Gly
65                  70                  75                  80

Glu Glu Leu Leu Ile Leu Asn Glu Ser Asp Ile Tyr Gly Val Leu Glu
                85                  90                  95

Ala
```

<210> SEQ ID NO 13
<211> LENGTH: 548
<212> TYPE: PRT
<213> ORGANISM: Oleispira antarctica
<220> FEATURE:
<223> OTHER INFORMATION: Cpn 60

<400> SEQUENCE: 13

```
Met Ala Ala Lys Asp Val Leu Phe Gly Asp Ser Ala Arg Ala Lys Met
1               5                   10                  15

Leu Val Gly Val Asn Ile Leu Ala Asp Ala Val Arg Val Thr Leu Gly
            20                  25                  30

Pro Lys Gly Arg Asn Val Val Ile Glu Lys Ser Phe Gly Ala Pro Ile
```

```
                    35                  40                  45
Ile Thr Lys Asp Gly Val Ser Val Ala Arg Glu Ile Glu Leu Lys Asp
 50                  55                  60
Lys Phe Glu Asn Met Gly Ala Gln Met Val Lys Glu Val Ala Ser Gln
 65                  70                  75                  80
Ala Asn Asp Gln Ala Gly Asp Gly Thr Thr Thr Ala Thr Val Leu Ala
                 85                  90                  95
Gln Ala Ile Ile Ser Glu Gly Leu Lys Ser Val Ala Ala Gly Met Asn
             100                 105                 110
Pro Met Asp Leu Lys Arg Gly Ile Asp Lys Ala Thr Ala Ala Val Val
         115                 120                 125
Ala Ala Ile Lys Glu Gln Ala Gln Pro Cys Leu Asp Thr Lys Ala Ile
     130                 135                 140
Ala Gln Val Gly Thr Ile Ser Ala Asn Ala Asp Glu Thr Val Gly Arg
 145                 150                 155                 160
Leu Ile Ala Glu Ala Met Glu Lys Val Gly Lys Glu Gly Val Ile Thr
                 165                 170                 175
Val Glu Glu Gly Lys Gly Leu Glu Asp Glu Leu Asp Val Val Glu Gly
             180                 185                 190
Met Gln Phe Asp Arg Gly Tyr Leu Ser Pro Tyr Phe Ile Asn Asn Gln
         195                 200                 205
Glu Lys Met Thr Val Glu Met Glu Asn Pro Leu Ile Leu Leu Val Asp
     210                 215                 220
Lys Lys Ile Asp Asn Leu Gln Glu Leu Leu Pro Ile Leu Glu Asn Val
 225                 230                 235                 240
Ala Lys Ser Gly Arg Pro Leu Leu Ile Val Ala Glu Asp Val Glu Gly
                 245                 250                 255
Gln Ala Leu Ala Thr Leu Val Val Asn Asn Leu Arg Gly Thr Phe Lys
             260                 265                 270
Val Ala Ala Val Lys Ala Pro Gly Phe Gly Asp Arg Arg Lys Ala Met
         275                 280                 285
Leu Gln Asp Leu Ala Ile Leu Thr Gly Gly Gln Val Ile Ser Glu Glu
     290                 295                 300
Leu Gly Met Ser Leu Glu Thr Ala Asp Pro Ser Ser Leu Gly Thr Ala
 305                 310                 315                 320
Ser Lys Val Val Ile Asp Lys Glu Asn Thr Val Ile Val Asp Gly Ala
                 325                 330                 335
Gly Thr Glu Ala Ser Val Asn Thr Arg Val Asp Gln Ile Arg Ala Glu
             340                 345                 350
Ile Glu Ser Ser Thr Ser Asp Tyr Asp Ile Glu Lys Leu Gln Glu Arg
         355                 360                 365
Val Ala Lys Leu Ala Gly Gly Val Ala Val Ile Lys Val Gly Ala Gly
     370                 375                 380
Ser Glu Met Glu Met Lys Glu Lys Lys Asp Arg Val Asp Asp Ala Leu
 385                 390                 395                 400
His Ala Thr Arg Ala Ala Val Glu Glu Gly Val Val Ala Gly Gly Gly
                 405                 410                 415
Val Ala Leu Ile Arg Ala Leu Ser Ser Val Thr Val Val Gly Asp Asn
             420                 425                 430
Glu Asp Gln Asn Val Gly Ile Ala Leu Ala Leu Arg Ala Met Glu Ala
         435                 440                 445
Pro Ile Arg Gln Ile Ala Gly Asn Ala Gly Ala Glu Gly Ser Val Val
     450                 455                 460
```

```
Val Asp Lys Val Lys Ser Gly Thr Gly Ser Phe Gly Phe Asn Ala Ser
465                 470                 475                 480

Thr Gly Glu Tyr Gly Asp Met Ile Ala Met Gly Ile Leu Asp Pro Ala
            485                 490                 495

Lys Val Thr Arg Ser Ser Leu Gln Ala Ala Ser Ile Ala Gly Leu
        500                 505                 510

Met Ile Thr Thr Glu Ala Met Val Ala Asp Ala Pro Val Glu Glu Gly
            515                 520                 525

Ala Gly Gly Met Pro Asp Met Gly Gly Met Gly Met Gly Gly Met
        530                 535                 540

Pro Gly Met Met
545

<210> SEQ ID NO 14
<211> LENGTH: 509
<212> TYPE: PRT
<213> ORGANISM: Rattus norvegicus
<220> FEATURE:
<223> OTHER INFORMATION: PDI protein, PDIA1_RAT

<400> SEQUENCE: 14

Met Leu Ser Arg Ala Leu Leu Cys Leu Ala Leu Ala Trp Ala Ala Arg
1               5                   10                  15

Val Gly Ala Asp Ala Leu Glu Glu Asp Asn Val Leu Val Leu Lys
            20                  25                  30

Lys Ser Asn Phe Ala Glu Ala Leu Ala Ala His Asn Tyr Leu Leu Val
        35                  40                  45

Glu Phe Tyr Ala Pro Trp Cys Gly His Cys Lys Ala Leu Ala Pro Glu
50                  55                  60

Tyr Ala Lys Ala Ala Ala Lys Leu Lys Ala Glu Gly Ser Glu Ile Arg
65                  70                  75                  80

Leu Ala Lys Val Asp Ala Thr Glu Glu Ser Asp Leu Ala Gln Gln Tyr
                85                  90                  95

Gly Val Arg Gly Tyr Pro Thr Ile Lys Phe Phe Lys Asn Gly Asp Thr
            100                 105                 110

Ala Ser Pro Lys Glu Tyr Thr Ala Gly Arg Glu Ala Asp Asp Ile Val
        115                 120                 125

Asn Trp Leu Lys Lys Arg Thr Gly Pro Ala Ala Thr Thr Leu Ser Asp
130                 135                 140

Thr Ala Ala Ala Glu Ser Leu Val Asp Ser Ser Glu Val Thr Val Ile
145                 150                 155                 160

Gly Phe Phe Lys Asp Ala Gly Ser Asp Ser Ala Lys Gln Phe Leu Leu
                165                 170                 175

Ala Ala Glu Ala Val Asp Asp Ile Pro Phe Gly Ile Thr Ser Asn Ser
            180                 185                 190

Asp Val Phe Ser Lys Tyr Gln Leu Asp Lys Asp Gly Val Val Leu Phe
        195                 200                 205

Lys Lys Phe Asp Glu Gly Arg Asn Asn Phe Glu Gly Glu Ile Thr Lys
210                 215                 220

Glu Lys Leu Leu Asp Phe Ile Lys His Asn Gln Leu Pro Leu Val Ile
225                 230                 235                 240

Glu Phe Thr Glu Gln Thr Ala Pro Lys Ile Phe Gly Gly Glu Ile Lys
                245                 250                 255

Thr His Ile Leu Leu Phe Leu Pro Lys Ser Val Ser Asp Tyr Asp Gly
            260                 265                 270

Lys Leu Ser Asn Phe Lys Lys Ala Ala Glu Gly Phe Lys Gly Lys Ile
```

```
              275                 280                 285
Leu Phe Ile Phe Ile Asp Ser Asp His Thr Asp Asn Gln Arg Ile Leu
290                 295                 300

Glu Phe Phe Gly Leu Lys Lys Glu Glu Cys Pro Ala Val Arg Leu Ile
305                 310                 315                 320

Thr Leu Glu Glu Glu Met Thr Lys Tyr Lys Pro Glu Ser Asp Glu Leu
                325                 330                 335

Thr Ala Glu Lys Ile Thr Gln Phe Cys His His Phe Leu Glu Gly Lys
            340                 345                 350

Ile Lys Pro His Leu Met Ser Gln Glu Leu Pro Glu Asp Trp Asp Lys
        355                 360                 365

Gln Pro Val Lys Val Leu Val Gly Lys Asn Phe Glu Glu Val Ala Phe
    370                 375                 380

Asp Glu Lys Lys Asn Val Phe Val Glu Phe Tyr Ala Pro Trp Cys Gly
385                 390                 395                 400

His Cys Lys Gln Leu Ala Pro Ile Trp Asp Lys Leu Gly Glu Thr Tyr
                405                 410                 415

Lys Asp His Glu Asn Ile Val Ile Ala Lys Met Asp Ser Thr Ala Asn
            420                 425                 430

Glu Val Glu Ala Val Lys Val His Ser Phe Pro Thr Leu Lys Phe Phe
        435                 440                 445

Pro Ala Ser Ala Asp Arg Thr Val Ile Asp Tyr Asn Gly Glu Arg Thr
    450                 455                 460

Leu Asp Gly Phe Lys Lys Phe Leu Glu Ser Gly Gly Gln Asp Gly Ala
465                 470                 475                 480

Gly Asp Asn Asp Asp Leu Asp Leu Glu Glu Ala Leu Glu Pro Asp Met
                485                 490                 495

Glu Glu Asp Asp Asp Gln Lys Ala Val Lys Asp Glu Leu
            500                 505

<210> SEQ ID NO 15
<211> LENGTH: 563
<212> TYPE: PRT
<213> ORGANISM: Saccharomyces cerevisiae
<220> FEATURE:
<223> OTHER INFORMATION: Ero1p

<400> SEQUENCE: 15

Met Arg Leu Arg Thr Ala Ile Ala Thr Leu Cys Leu Thr Ala Phe Thr
1               5                   10                  15

Ser Ala Thr Ser Asn Asn Ser Tyr Ile Ala Thr Asp Gln Thr Gln Asn
            20                  25                  30

Ala Phe Asn Asp Thr His Phe Cys Lys Val Asp Arg Asn Asp His Val
        35                  40                  45

Ser Pro Ser Cys Asn Val Thr Phe Asn Glu Leu Asn Ala Ile Asn Glu
    50                  55                  60

Asn Ile Arg Asp Asp Leu Ser Ala Leu Leu Lys Ser Asp Phe Phe Lys
65                  70                  75                  80

Tyr Phe Arg Leu Asp Leu Tyr Lys Gln Cys Ser Phe Trp Asp Ala Asn
                85                  90                  95

Asp Gly Leu Cys Leu Asn Arg Ala Cys Ser Val Asp Val Val Glu Asp
            100                 105                 110

Trp Asp Thr Leu Pro Glu Tyr Trp Gln Pro Glu Ile Leu Gly Ser Phe
        115                 120                 125

Asn Asn Asp Thr Met Lys Glu Ala Asp Asp Ser Asp Asp Glu Cys Lys
    130                 135                 140
```

```
Phe Leu Asp Gln Leu Cys Gln Thr Ser Lys Lys Pro Val Asp Ile Glu
145                 150                 155                 160

Asp Thr Ile Asn Tyr Cys Asp Val Asn Asp Phe Asn Gly Lys Asn Ala
            165                 170                 175

Val Leu Ile Asp Leu Thr Ala Asn Pro Glu Arg Phe Thr Gly Tyr Gly
        180                 185                 190

Gly Lys Gln Ala Gly Gln Ile Trp Ser Thr Ile Tyr Gln Asp Asn Cys
    195                 200                 205

Phe Thr Ile Gly Glu Thr Gly Glu Ser Leu Ala Lys Asp Ala Phe Tyr
210                 215                 220

Arg Leu Val Ser Gly Phe His Ala Ser Ile Gly Thr His Leu Ser Lys
225                 230                 235                 240

Glu Tyr Leu Asn Thr Lys Thr Gly Lys Trp Glu Pro Asn Leu Asp Leu
            245                 250                 255

Phe Met Ala Arg Ile Gly Asn Phe Pro Asp Arg Val Thr Asn Met Tyr
        260                 265                 270

Phe Asn Tyr Ala Val Val Ala Lys Ala Leu Trp Lys Ile Gln Pro Tyr
    275                 280                 285

Leu Pro Glu Phe Ser Phe Cys Asp Leu Val Asn Lys Glu Ile Lys Asn
290                 295                 300

Lys Met Asp Asn Val Ile Ser Gln Leu Asp Thr Lys Ile Phe Asn Glu
305                 310                 315                 320

Asp Leu Val Phe Ala Asn Asp Leu Ser Leu Thr Leu Lys Asp Glu Phe
            325                 330                 335

Arg Ser Arg Phe Lys Asn Val Thr Lys Ile Met Asp Cys Val Gln Cys
        340                 345                 350

Asp Arg Cys Arg Leu Trp Gly Lys Ile Gln Thr Thr Gly Tyr Ala Thr
    355                 360                 365

Ala Leu Lys Ile Leu Phe Glu Ile Asn Asp Ala Asp Glu Phe Thr Lys
370                 375                 380

Gln His Ile Val Gly Lys Leu Thr Lys Tyr Glu Leu Ile Ala Leu Leu
385                 390                 395                 400

Gln Thr Phe Gly Arg Leu Ser Glu Ser Ile Glu Ser Val Asn Met Phe
            405                 410                 415

Glu Lys Met Tyr Gly Lys Arg Leu Asn Gly Ser Glu Asn Arg Leu Ser
        420                 425                 430

Ser Phe Phe Gln Asn Asn Phe Phe Asn Ile Leu Lys Glu Ala Gly Lys
    435                 440                 445

Ser Ile Arg Tyr Thr Ile Glu Asn Ile Asn Ser Thr Lys Glu Gly Lys
450                 455                 460

Lys Lys Thr Asn Asn Ser Gln Ser His Val Phe Asp Asp Leu Lys Met
465                 470                 475                 480

Pro Lys Ala Glu Ile Val Pro Arg Pro Ser Asn Gly Thr Val Asn Lys
            485                 490                 495

Trp Lys Lys Ala Trp Asn Thr Glu Val Asn Asn Val Leu Glu Ala Phe
        500                 505                 510

Arg Phe Ile Tyr Arg Ser Tyr Leu Asp Leu Pro Arg Asn Ile Trp Glu
    515                 520                 525

Leu Ser Leu Met Lys Val Tyr Lys Phe Trp Asn Lys Phe Ile Gly Val
530                 535                 540

Ala Asp Tyr Val Ser Glu Glu Thr Arg Glu Pro Ile Ser Tyr Lys Leu
545                 550                 555                 560

Asp Ile Gln
```

<210> SEQ ID NO 16
<211> LENGTH: 701
<212> TYPE: PRT
<213> ORGANISM: Saccharomyces cerevisiae
<220> FEATURE:
<223> OTHER INFORMATION: Pdi1p

<400> SEQUENCE: 16

```
Met Lys Met Asn Leu Lys Arg Leu Val Val Thr Phe Phe Ser Cys Ile
1               5                   10                  15

Thr Phe Leu Leu Lys Phe Thr Ile Ala Ala Glu Pro Pro Glu Gly
            20                  25                  30

Phe Pro Glu Pro Leu Asn Pro Thr Asn Phe Lys Glu Glu Leu Ser Lys
        35                  40                  45

Gly Leu His Ile Ile Asp Phe Tyr Ser Pro Tyr Cys Pro His Cys Lys
    50                  55                  60

His Leu Ala Pro Val Trp Met Glu Thr Trp Glu Glu Phe Lys Glu Glu
65                  70                  75                  80

Ser Lys Thr Leu Asn Ile Thr Phe Ser Gln Val Asn Cys Ile Glu Ser
                85                  90                  95

Ala Asp Leu Cys Gly Asp Glu Asn Ile Glu Tyr Phe Pro Glu Ile Arg
            100                 105                 110

Leu Tyr Asn Pro Ser Gly Tyr Ile Lys Ser Phe Thr Glu Thr Pro Arg
        115                 120                 125

Thr Lys Glu Ser Leu Ile Ala Phe Ala Arg Arg Glu Ser Met Asp Pro
    130                 135                 140

Asn Asn Leu Asp Thr Asp Leu Asp Ser Ala Lys Ser Glu Ser Gln Tyr
145                 150                 155                 160

Leu Glu Gly Phe Asp Phe Leu Glu Leu Ile Ala Gly Lys Ala Thr Arg
                165                 170                 175

Pro His Leu Val Ser Phe Trp Pro Thr Lys Asp Met Lys Asn Ser Asp
            180                 185                 190

Asp Ser Leu Glu Phe Lys Asn Cys Asp Lys Cys His Glu Phe Gln Arg
        195                 200                 205

Thr Trp Lys Ile Ile Ser Arg Gln Leu Ala Val Asp Asp Ile Asn Thr
    210                 215                 220

Gly His Val Asn Cys Glu Ser Asn Pro Thr Ile Cys Glu Glu Leu Gly
225                 230                 235                 240

Phe Gly Asp Leu Val Lys Ile Thr Asn His Arg Ala Asp Arg Glu Pro
                245                 250                 255

Lys Val Ala Leu Val Leu Pro Asn Lys Thr Ser Asn Asn Leu Phe Asp
            260                 265                 270

Tyr Pro Asn Gly Tyr Ser Ala Lys Ser Asp Gly Tyr Val Asp Phe Ala
        275                 280                 285

Arg Arg Thr Phe Thr Asn Ser Lys Phe Pro Asn Ile Thr Glu Gly Glu
    290                 295                 300

Leu Glu Lys Lys Ala Asn Arg Asp Ile Asp Phe Leu Gln Glu Arg Gly
305                 310                 315                 320

Arg Val Thr Asn Asn Asp Ile His Leu Val Phe Ser Tyr Asp Pro Glu
                325                 330                 335

Thr Val Val Ile Glu Asp Phe Asp Ile Leu Glu Tyr Leu Ile Glu Pro
            340                 345                 350

Leu Ser Lys Ile Pro Asn Ile Tyr Leu His Gln Ile Asp Lys Asn Leu
        355                 360                 365
```

Ile Asn Leu Ser Arg Asn Leu Phe Gly Arg Met Tyr Glu Lys Ile Asn
            370                 375                 380

Tyr Asp Ala Ser Gln Thr Gln Lys Val Phe Asn Lys Glu Tyr Phe Thr
385                 390                 395                 400

Met Asn Thr Val Thr Gln Leu Pro Thr Phe Phe Met Phe Lys Asp Gly
            405                 410                 415

Asp Pro Ile Ser Tyr Val Phe Pro Gly Tyr Ser Thr Thr Glu Met Arg
            420                 425                 430

Asn Ile Asp Ala Ile Met Asp Trp Val Lys Lys Tyr Ser Asn Pro Leu
            435                 440                 445

Val Thr Glu Val Asp Ser Asn Leu Lys Lys Leu Ile Ser Phe Gln
            450                 455                 460

Thr Lys Ser Tyr Ser Asp Leu Ala Ile Gln Leu Ile Ser Ser Thr Asp
465                 470                 475                 480

His Lys His Ile Lys Gly Ser Asn Lys Leu Ile Lys Asn Leu Leu Leu
            485                 490                 495

Ala Ser Trp Glu Tyr Glu His Ile Arg Met Glu Asn Asn Phe Glu Glu
            500                 505                 510

Ile Asn Glu Arg Arg Ala Arg Lys Ala Asp Gly Ile Lys Lys Ile Lys
            515                 520                 525

Glu Lys Lys Ala Pro Ala Asn Lys Ile Val Asp Lys Met Arg Glu Glu
530                 535                 540

Ile Pro His Met Asp Gln Lys Lys Leu Leu Leu Gly Tyr Leu Asp Ile
545                 550                 555                 560

Ser Lys Glu Lys Asn Phe Phe Arg Lys Tyr Gly Ile Thr Gly Glu Tyr
            565                 570                 575

Lys Ile Gly Asp Val Ile Ile Ile Asp Lys Ser Asn Asn Tyr Tyr Tyr
            580                 585                 590

Asn Lys Asp Asn Phe Gly Asn Ser Leu Thr Ser Asn Asn Pro Gln Leu
            595                 600                 605

Leu Arg Glu Ala Phe Val Ser Leu Asn Ile Pro Ser Lys Ala Leu Tyr
            610                 615                 620

Ser Ser Lys Leu Lys Gly Arg Leu Ile Asn Ser Pro Phe His Asn Val
625                 630                 635                 640

Leu Ser Phe Leu Asp Ile Ile His Gly Asn Gly Met Pro Gly Tyr Leu
            645                 650                 655

Ile Val Ile Val Leu Phe Ile Ala Ile Leu Lys Gly Pro Ser Ile Tyr
            660                 665                 670

Arg Arg Tyr Lys Val Arg Lys His Tyr Arg Ala Lys Arg Asn Ala Val
            675                 680                 685

Gly Ile Leu Gly Asn Met Glu Lys Lys Lys Asn Gln Asp
            690                 695                 700

<210> SEQ ID NO 17
<211> LENGTH: 176
<212> TYPE: PRT
<213> ORGANISM: Escherichia coli
<220> FEATURE:
<223> OTHER INFORMATION: DsbB protein

<400> SEQUENCE: 17

Met Leu Arg Phe Leu Asn Gln Cys Ser Gln Gly Arg Gly Ala Trp Leu
1               5                   10                  15

Leu Met Ala Phe Thr Ala Leu Ala Leu Glu Leu Thr Ala Leu Trp Phe
            20                  25                  30

Gln His Val Met Leu Leu Lys Pro Cys Val Leu Cys Ile Tyr Glu Arg

```
                 35                  40                  45
Cys Ala Leu Phe Gly Val Leu Gly Ala Ala Leu Ile Gly Ala Ile Ala
 50                  55                  60
Pro Lys Thr Pro Leu Arg Tyr Val Ala Met Val Ile Trp Leu Tyr Ser
 65                  70                  75                  80
Ala Phe Arg Gly Val Gln Leu Thr Tyr Glu His Thr Met Leu Gln Leu
                 85                  90                  95
Tyr Pro Ser Pro Phe Ala Thr Cys Asp Phe Met Val Arg Phe Pro Glu
                100                 105                 110
Trp Leu Pro Leu Asp Lys Trp Val Pro Gln Val Phe Val Ala Ser Gly
                115                 120                 125
Asp Cys Ala Glu Arg Gln Trp Asp Phe Leu Gly Leu Glu Met Pro Gln
                130                 135                 140
Trp Leu Leu Gly Ile Phe Ile Ala Tyr Leu Ile Val Ala Val Leu Val
145                 150                 155                 160
Val Ile Ser Gln Pro Phe Lys Ala Lys Lys Arg Asp Leu Phe Gly Arg
                165                 170                 175

<210> SEQ ID NO 18
<211> LENGTH: 208
<212> TYPE: PRT
<213> ORGANISM: Escherichia coli
<220> FEATURE:
<223> OTHER INFORMATION: DsbA protein

<400> SEQUENCE: 18

Met Lys Lys Ile Trp Leu Ala Leu Ala Gly Leu Val Leu Ala Phe Ser
  1               5                  10                  15
Ala Ser Ala Ala Gln Tyr Glu Asp Gly Lys Gln Tyr Thr Thr Leu Glu
                 20                  25                  30
Lys Pro Val Ala Gly Ala Pro Gln Val Leu Glu Phe Phe Ser Phe Phe
                 35                  40                  45
Cys Pro His Cys Tyr Gln Phe Glu Glu Val Leu His Ile Ser Asp Asn
 50                  55                  60
Val Lys Lys Lys Leu Pro Glu Gly Val Lys Met Thr Lys Tyr His Val
 65                  70                  75                  80
Asn Phe Met Gly Gly Asp Leu Gly Lys Asp Leu Thr Gln Ala Trp Ala
                 85                  90                  95
Val Ala Met Ala Leu Gly Val Glu Asp Lys Val Thr Val Pro Leu Phe
                100                 105                 110
Glu Gly Val Gln Lys Thr Gln Thr Ile Arg Ser Ala Ser Asp Ile Arg
                115                 120                 125
Asp Val Phe Ile Asn Ala Gly Ile Lys Gly Glu Glu Tyr Asp Ala Ala
                130                 135                 140
Trp Asn Ser Phe Val Val Lys Ser Leu Val Ala Gln Gln Glu Lys Ala
145                 150                 155                 160
Ala Ala Asp Val Gln Leu Arg Gly Val Pro Ala Met Phe Val Asn Gly
                165                 170                 175
Lys Tyr Gln Leu Asn Pro Gln Gly Met Asp Thr Ser Asn Met Asp Val
                180                 185                 190
Phe Val Gln Gln Tyr Ala Asp Thr Val Lys Tyr Leu Ser Glu Lys Lys
                195                 200                 205

<210> SEQ ID NO 19
<211> LENGTH: 236
<212> TYPE: PRT
<213> ORGANISM: Escherichia coli
```

<220> FEATURE:
<223> OTHER INFORMATION: DsbC protein

<400> SEQUENCE: 19

```
Met Lys Lys Gly Phe Met Leu Phe Thr Leu Leu Ala Ala Phe Ser Gly
1               5                   10                  15

Phe Ala Gln Ala Asp Asp Ala Ala Ile Gln Gln Thr Leu Ala Lys Met
            20                  25                  30

Gly Ile Lys Ser Ser Asp Ile Gln Pro Ala Pro Val Ala Gly Met Lys
        35                  40                  45

Thr Val Leu Thr Asn Ser Gly Val Leu Tyr Ile Thr Asp Asp Gly Lys
    50                  55                  60

His Ile Ile Gln Gly Pro Met Tyr Asp Val Ser Gly Thr Ala Pro Val
65                  70                  75                  80

Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
        115                 120                 125

Ala Asp Tyr Asn Ala Leu Gly Ile Thr Val Arg Tyr Leu Ala Phe Pro
    130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
            180                 185                 190

Leu Gly Val Gln Leu Gly Val Ser Gly Thr Pro Ala Val Val Leu Ser
        195                 200                 205

Asn Gly Thr Leu Val Pro Gly Tyr Gln Pro Pro Lys Glu Met Lys Glu
    210                 215                 220

Phe Leu Asp Glu His Gln Lys Met Thr Ser Gly Lys
225                 230                 235
```

<210> SEQ ID NO 20
<211> LENGTH: 565
<212> TYPE: PRT
<213> ORGANISM: Escherichia coli
<220> FEATURE:
<223> OTHER INFORMATION: DsbD protein

<400> SEQUENCE: 20

```
Met Ala Gln Arg Ile Phe Thr Leu Ile Leu Leu Leu Cys Ser Thr Ser
1               5                   10                  15

Val Phe Ala Gly Leu Phe Asp Ala Pro Gly Arg Ser Gln Phe Val Pro
            20                  25                  30

Ala Asp Gln Ala Phe Ala Phe Asp Phe Gln Gln Asn Gln His Asp Leu
        35                  40                  45

Asn Leu Thr Trp Gln Ile Lys Asp Gly Tyr Tyr Leu Tyr Arg Lys Gln
    50                  55                  60

Ile Arg Ile Thr Pro Glu His Ala Lys Ile Ala Asp Val Gln Leu Pro
65                  70                  75                  80

Gln Gly Val Trp His Glu Asp Glu Phe Tyr Gly Lys Ser Glu Ile Tyr
                85                  90                  95

Arg Asp Arg Leu Thr Leu Pro Val Thr Ile Asn Gln Ala Ser Ala Gly
            100                 105                 110
```

```
Ala Thr Leu Thr Val Thr Tyr Gln Gly Cys Ala Asp Ala Gly Phe Cys
            115                 120                 125

Tyr Pro Pro Glu Thr Lys Thr Val Pro Leu Ser Glu Val Val Ala Asn
            130                 135                 140

Asn Ala Ala Pro Gln Pro Val Ser Val Pro Gln Glu Gln Pro Thr
145                 150                 155                 160

Ala Gln Leu Pro Phe Ser Ala Leu Trp Ala Leu Leu Ile Gly Ile Gly
            165                 170                 175

Ile Ala Phe Thr Pro Cys Val Leu Pro Met Tyr Pro Leu Ile Ser Gly
            180                 185                 190

Ile Val Leu Gly Gly Lys Gln Arg Leu Ser Thr Ala Arg Ala Leu Leu
            195                 200                 205

Leu Thr Phe Ile Tyr Val Gln Gly Met Ala Leu Thr Tyr Thr Ala Leu
            210                 215                 220

Gly Leu Val Val Ala Ala Gly Leu Gln Phe Gln Ala Ala Leu Gln
225                 230                 235                 240

His Pro Tyr Val Leu Ile Gly Leu Ala Ile Val Phe Thr Leu Leu Ala
            245                 250                 255

Met Ser Met Phe Gly Leu Phe Thr Leu Gln Leu Pro Ser Ser Leu Gln
            260                 265                 270

Thr Arg Leu Thr Leu Met Ser Asn Arg Gln Gln Gly Gly Ser Pro Gly
            275                 280                 285

Gly Val Phe Val Met Gly Ala Ile Ala Gly Leu Ile Cys Ser Pro Cys
            290                 295                 300

Thr Thr Ala Pro Leu Ser Ala Ile Leu Leu Tyr Ile Ala Gln Ser Gly
305                 310                 315                 320

Asn Met Trp Leu Gly Gly Gly Thr Leu Tyr Leu Tyr Ala Leu Gly Met
            325                 330                 335

Gly Leu Pro Leu Met Leu Ile Thr Val Phe Gly Asn Arg Leu Leu Pro
            340                 345                 350

Lys Ser Gly Pro Trp Met Glu Gln Val Lys Thr Ala Phe Gly Phe Val
            355                 360                 365

Ile Leu Ala Leu Pro Val Phe Leu Leu Glu Arg Val Ile Gly Asp Val
            370                 375                 380

Trp Gly Leu Arg Leu Trp Ser Ala Leu Gly Val Ala Phe Phe Gly Trp
385                 390                 395                 400

Ala Phe Ile Thr Ser Leu Gln Ala Lys Arg Gly Trp Met Arg Ile Val
            405                 410                 415

Gln Ile Ile Leu Leu Ala Ala Ala Leu Val Ser Val Arg Pro Leu Gln
            420                 425                 430

Asp Trp Ala Phe Gly Ala Thr His Thr Ala Gln Thr Gln Thr His Leu
            435                 440                 445

Asn Phe Thr Gln Ile Lys Thr Val Asp Glu Leu Asn Gln Ala Leu Val
            450                 455                 460

Glu Ala Lys Gly Lys Pro Val Met Leu Asp Leu Tyr Ala Asp Trp Cys
465                 470                 475                 480

Val Ala Cys Lys Glu Phe Glu Lys Tyr Thr Phe Ser Asp Pro Gln Val
            485                 490                 495

Gln Lys Ala Leu Ala Asp Thr Val Leu Leu Gln Ala Asn Val Thr Ala
            500                 505                 510

Asn Asp Ala Gln Asp Val Ala Leu Leu Lys His Leu Asn Val Leu Gly
            515                 520                 525

Leu Pro Thr Ile Leu Phe Phe Asp Gly Gln Gly Gln Glu His Pro Gln
```

```
                                  530                 535                 540
Ala Arg Val Thr Gly Phe Met Asp Ala Glu Thr Phe Ser Ala His Leu
545                 550                 555                 560

Arg Asp Arg Gln Pro
                565

<210> SEQ ID NO 21
<211> LENGTH: 268
<212> TYPE: PRT
<213> ORGANISM: Escherichia coli
<220> FEATURE:
<223> OTHER INFORMATION: DsbG protein

<400> SEQUENCE: 21

Met Thr Val Ile Gly Tyr Ala Phe Tyr Ser Thr Phe Ala Leu Thr Glu
1               5                   10                  15

Lys Asp Lys Leu Met Leu Lys Lys Ile Leu Leu Ala Leu Leu Pro
                20                  25                  30

Ala Ile Ala Phe Ala Glu Glu Leu Pro Ala Pro Val Lys Ala Ile Glu
                35                  40                  45

Lys Gln Gly Ile Thr Ile Ile Lys Thr Phe Asp Ala Pro Gly Gly Met
50                  55                  60

Lys Gly Tyr Leu Gly Lys Tyr Gln Asp Met Gly Val Thr Ile Tyr Leu
65                  70                  75                  80

Thr Pro Asp Gly Lys His Ala Ile Ser Gly Tyr Met Tyr Asn Glu Lys
                85                  90                  95

Gly Glu Asn Leu Ser Asn Thr Leu Ile Glu Lys Glu Ile Tyr Ala Pro
                100                 105                 110

Ala Gly Arg Glu Met Trp Gln Arg Met Glu Gln Ser His Trp Leu Leu
                115                 120                 125

Asp Gly Lys Lys Asp Ala Pro Val Ile Val Tyr Val Phe Ala Asp Pro
130                 135                 140

Phe Cys Pro Tyr Cys Lys Gln Phe Trp Gln Gln Ala Arg Pro Trp Val
145                 150                 155                 160

Asp Ser Gly Lys Val Gln Leu Arg Thr Leu Leu Val Gly Val Ile Lys
                165                 170                 175

Pro Glu Ser Pro Ala Thr Ala Ala Ile Leu Ala Ser Lys Asp Pro
                180                 185                 190

Ala Lys Thr Trp Gln Gln Tyr Glu Ala Ser Gly Gly Lys Leu Lys Leu
                195                 200                 205

Asn Val Pro Ala Asn Val Ser Thr Glu Gln Met Lys Val Leu Ser Asp
210                 215                 220

Asn Glu Lys Leu Met Asp Asp Leu Gly Ala Asn Val Thr Pro Ala Ile
225                 230                 235                 240

Tyr Tyr Met Ser Lys Glu Asn Thr Leu Gln Gln Ala Val Gly Leu Pro
                245                 250                 255

Asp Gln Lys Thr Leu Asn Ile Ile Met Gly Asn Lys
                260                 265

<210> SEQ ID NO 22
<211> LENGTH: 8
<212> TYPE: PRT
<213> ORGANISM: Artificial Sequence
<220> FEATURE:
<223> OTHER INFORMATION: synthetic FLAG tag

<400> SEQUENCE: 22

Asp Tyr Lys Asp Asp Asp Asp Lys
```

```
<210> SEQ ID NO 23
<211> LENGTH: 5
<212> TYPE: PRT
<213> ORGANISM: Artificial Sequence
<220> FEATURE:
<223> OTHER INFORMATION: synthetic DDDDK (EC5) tag

<400> SEQUENCE: 23

Asp Asp Asp Asp Lys
1               5

<210> SEQ ID NO 24
<211> LENGTH: 6
<212> TYPE: PRT
<213> ORGANISM: Artificial Sequence
<220> FEATURE:
<223> OTHER INFORMATION: synthetic 6 residue EYMPME peptide

<400> SEQUENCE: 24

Glu Tyr Met Pro Met Glu
1               5
```